United States Patent [19]
Bradshaw et al.

[11] Patent Number: 5,403,898
[45] Date of Patent: Apr. 4, 1995

[54] SINGLE ARM ATTACHED CYCLODEXTRIN POLYSILOXANES AND USE THEREOF AS CHIRAL STATIONARY PHASES IN CHROMATOGRAPHIC SEPARATION OF ENANTIOMERS

[75] Inventors: Jerald S. Bradshaw, Provo; Milton L. Lee, Pleasant Grove; Bryant E. Rossiter, Provo, all of Utah

[73] Assignee: Brigham Young University, Provo, Utah

[21] Appl. No.: 163,870

[22] Filed: Dec. 7, 1993

Related U.S. Application Data

[63] Continuation-in-part of Ser. No. 878,157, May 4, 1992, Pat. No. 5,268,442.

[51] Int. Cl.$^6$ ............................................. C08F 283/00
[52] U.S. Cl. ...................... 525/474; 527/300; 527/312; 527/313; 527/314; 536/103; 528/15; 528/25; 528/26; 528/28; 528/29; 528/30; 528/31
[58] Field of Search ................ 525/474; 527/300, 312, 527/313, 314; 536/103; 528/25, 26, 28, 29, 30, 31, 15

[56] References Cited

U.S. PATENT DOCUMENTS

| | | | |
|---|---|---|---|
| 5,248,675 | 9/1993 | Kurita et al. | 536/103 |
| 5,262,404 | 11/1993 | Weisz et al. | 536/103 |
| 5,268,442 | 12/1993 | Bradshaw et al. | 528/31 |

*Primary Examiner*—Melvyn I. Marquis
*Attorney, Agent, or Firm*—Thorpe, North & Western

[57] ABSTRACT

Cyclodextrin containing polymeric siloxanes wherein the cyclodextrin is connected to the polymeric siloxane by a single linking member connected to the 2, 3 or 6-position of the cyclodextrin are disclosed. These polymers are chemically and thermally stable to gas, supercritical fluid chromatographic conditions. The single arm attachment provides cyclodextrin containing polysiloxane polymers having synthesis reproducibility from batch to batch resulting in consistent chromatographic performance of the resulting chiral phases. The use of such polymers as chiral stationary phases in analytical and preparative gas, supercritical fluid and liquid chromatographic separations, and particularly for analysis of enantiomeric and other stereoisomeric mixtures of various substances is shown.

26 Claims, 13 Drawing Sheets

SINGLE ARM ATTACHED CYCLODEXTRIN POLYSILOXANES AND USE THEREOF AS CHIRAL STATIONARY PHASES IN CHROMATOGRAPHIC SEPARATION OF ENANTIOMERS

This application is a continuation-in part of application Ser. No. 07/878,157, filed May 4, 1992, now U.S. Pat. No. 5,268,442.

BACKGROUND OF THE INVENTION

1. Field of Invention

The present invention relates to novel chiral polymers comprising a peralkyl cyclodextrin bound to polysiloxane by means of a single spacer arm and the use of such polymers as chiral stationary phases in analytical and preparative gas, supercritical fluid and liquid chromatographic separations. More particularly, this invention relates to novel chiral polymers a peralkylated cyclodextrin, preferably a β-cyclodextrin, bound to a linear polysiloxane by means of a single spacer arm which can have various lengths and compositions. This invention also relates to the use of these cyclodextrin containing polysiloxane polymers for analysis of enantiomeric and other stereoisomeric mixtures of various substances. This invention relates as well to the use of either open tubular column surface-bonded or packed column particle-bound chiral cyclodextrin polymeric siloxane materials, prepared by coating and immobilizing by chemical reaction or heating the chiral polymeric siloxanes on the desired column or particle surface for gas, supercritical fluid and liquid chromatography separations, and the separation of enantiomeric and other stereoisomeric mixtures of various structures using these materials.

2. Prior Art

Analytical separation of enantiomers has become very important in light of interest in the resolution and enantiomeric purity of drugs. *Chem. Eng. News,* 1990, Mar. 19, 38; Stinson, S.C. *Chem. Eng. News,* 1992, Sep. 28, 46. The use of chiral stationary phases (CSPs) in chromatography is the most convenient method to determine enantiomeric purity. Allenmark, S. G. *Chromatographic Enantioseparations: Methods and Applications,* 2nd ed., Prentice Hall, N.J., 19991. In recent years, the use of O-derivatized cyclodextrins as CSPs in capillary gas chromatography (GC) and supercritical fluid chromatography (SFC) has become a powerful tool in modern enantiomer analysis. Schurig, et al., *Angew. Chem. Int. Ed. Engl.* 1990, 29, 939; Koen de Vries et al., *J. High Resolut. Chromatogr.* 1992, 15, 499; Dietrich, et al., *J. High Resolut. Chromatogr.* 1992, 15, 590; Reiher, et al., *J. High Resolut. Chromatogr.* 1992, 15, 346 and Schurig, et al., *J. High Resolut. Chromatogr.* 1991, 14, 58. Most of the stationary phases derived from cyclodextrin are prepared by diluting the relevant cyclodextrin derivative in polysiloxane in order to obtain selective chiral separations at temperatures below the melting point of the pure cyclodextrin derivative. The state of the art in this field has been reviewed by Schurig, et al., *Angew. Chem. Int. Ed. Engl.* 1990, 29, 939. A few cyclodextrin stationary phases have been prepared by chemically bonding permethylated alkenyl-substituted β-cyclodextrin to a polysiloxane backbone by a hydrosilylation reaction. Schurig, et al., *J. High Resolut. Chromatogr.* 1991, 14, 58; Schurig, et al., *J. High Resolut. Chromatogr.* 1990, 13, 713 and Fischer, et al., *Angew. Chem. Int. Ed. Engl.* 1990, 29, 427. In these cases, the permethylated alkenyl-substituted β-cyclodextrins were a mixture of cyclodextrins containing 1–7 alkenyl group(s) on the rim of the cyclodextrin instead of a pure monoalkenyl-substituted compound. Because the number of connecting alkenyl groups on the rim of the cyclodextrin may vary from molecule to molecule, reproducibility or uniformity of product is not assured from batch to batch and results of separations of enantiomers may also vary.

Chiral copolymers, wherein the chiral portion of the copolymer can be a cyclodextrin are disclosed and claimed in copending patent application Ser. No. 07/878,157 filed May 4, 1992 which has been allowed and is awaiting issuance.

OBJECTS AND BRIEF SUMMARY OF THE INVENTION

It is an object of the present invention to reproducibly prepare quality chiral cyclodextrin phases for capillary SFC and GC having wide applicability and excellent enantioselectivity properties.

It is also an object of this invention to provide a series of cyclodextrins bound to polysiloxane by means of one spacer arm.

Another object of this invention is to provide cyclodextrin-containing phases yielding remarkable enantiomeric resolution of a variety of chiral organic solutes in both capillary SFC and GC.

These and other objectives and features of the present invention will be more fully apparent from the following description and appended claims, taken in conjunction with the accompanying drawings. However, in summary, the above stated objectives may be accomplished through the use of chiral cyclodextrin containing polymeric siloxanes wherein the cyclodextrin moiety is attached to the polysiloxane backbone by means of a single point of attachement and having the structure given below in Formulas I and II. In Formula I the cyclodextrin is attached at the small rim via the 6 position to the polysiloxane backbone. In Formula II the cyclodextrin is attached at the large rim via the 2 or 3 positions to the polysiloxane backbone.

These polymers result in chiral phases having high resolution, increased solute diffusion and higher separation efficiency as compared to cyclodextrins attached at multiple points to the polymer backbone. The present invention provides cyclodextrin containing polysiloxane polymers having synthesis reproducibility from batch to batch resulting in consistent chromatographic performance of the resulting chiral phases.

BRIEF DESCRIPTION OF THE DRAWINGS

All chromatograms shown are of separations on a stationary phase made in accordance with the present invention. These exemplify the ability of various embodiments of the invention to resolve enantiomers.

DETAILED DESCRIPTION OF THE PREFERRED EMBODIMENTS

Figure 1:
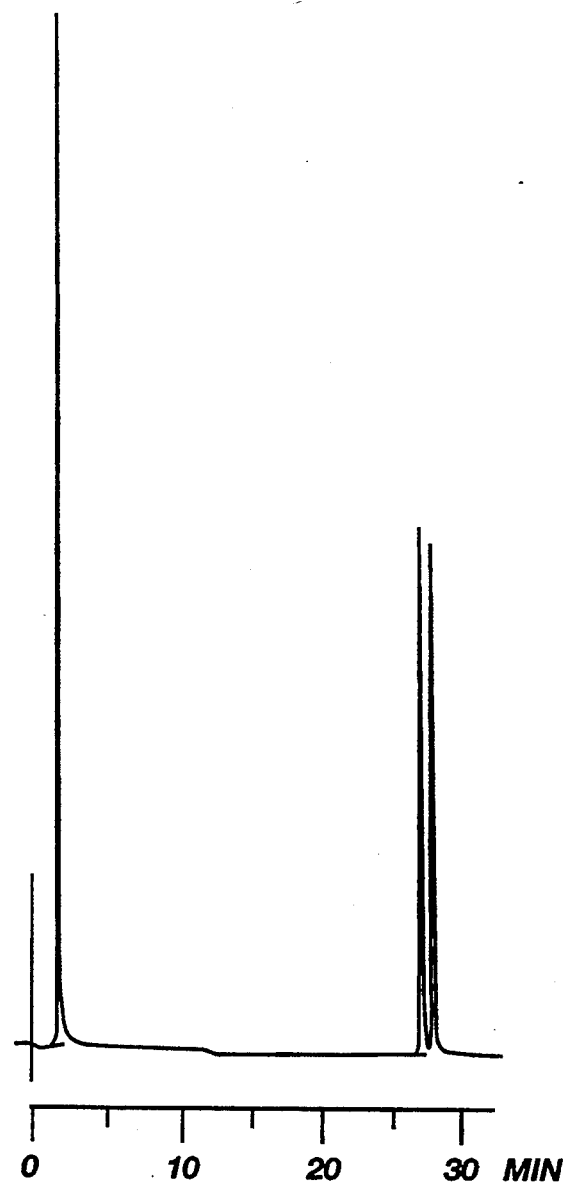
FIG. 1. Shows the GC separation of mandelic acid methyl ester enantiomers on the β-cyclodextrin-bound polysiloxane stationary phase of Example 21. Conditions: 30 m×250 μm i.d. fused silica column, 0.25 μm film thickness; 120° C.; helium carrier gas; FID (Flame Ionization Detector).

The cyclodextrin polysiloxanes of Formulas I and II form the basis of this invention wherein the cyclodextrin is attached to the polysiloxane backbone by a single spacer connection.

The cyclodextrin polysiloxanes of Formula I have the following general formula (Formula I):

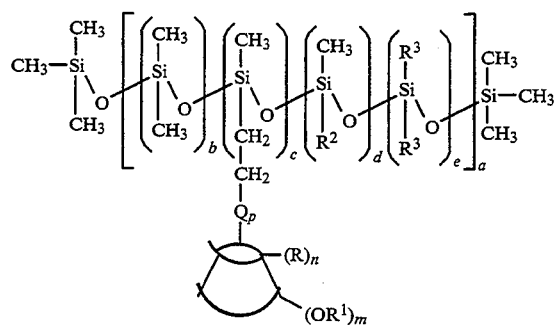

where n is an integer of 5 to 7, m is an integer of 12 to 16, p is 0 or 1, a is a numerical value of between about i to 10 and does not necessarily have to represent a whole integer, b is an integer of 20 to 150, c is an integer of 1 to 20, with the proviso that the ratio of b to c is at least 2:1 and may vary as high as 150:1, d is an integer of 0 to 5 and e is an integer of 0 to 5. R is a member selected from the group consisting of $CH_3$, $CH_2OR^1$, $CH_2O(CH_2)_xOR^1$, $CH_2O=Ar=O=R^1$, $CH_2O(CH_2CH_2O)_xR^1$ and $CH_2OC(O)R^1$ where $R^1$ is a member selected from the group consisting of alkyl, aralkyl, aryl and alkaryl. Q is a member selected from the group consisting of $CH_2(CH_2)_x$, $CH_2X(CH_2)_x$, $CH_2X—(CH_2)_x—XCH_2$, $CH_2X—(CH_2)_x—C(O)XCH_2$, $CH_2X—C(O)(CH_2)_x—XCH_2$, $CH_2X—Ar—XCH_2$, $CH_2X—(CH_2)_x—Ar—XCH_2$, $CH_2X—AR—(CH_2)_x-—XCH_2$, $CH_2X—(CH_2)_x—Ar—(CH_2)_x—XCH$, $CH_2X—Ar—C(O)XCH_2$, $CH_2X—(CH_2)_x—Ar—C(O)XCH_2$, $CH_2X—Ar—(CH_2)_x—C(O)XCH_2$, $CH_2X—(CH_2)_x—Ar—(CH_2)_x—C(O)XCH_2$, $CH_2XC(O)—Ar—XCH_2$, $CH_2XC(O)—(CH_2)_x-—Ar—XCH_2$, $CH_2XC(O)—Ar—(CH_2)_x—XCH_2$ and $CH_2XC(O)—(CH_2)_x—Ar—(CH_2)—XCH_2$. X is an integer of between 1 and 10. X is a member selected from the group consisting of O, S, or $NR^4$ where $R^4$ is H or $R^1$. Ar, aryl and the aryl portions of alkaryl and aralkyl represents an aromatic ring selected from the group consisting of benzene, thiophene, furan, pyridine, pyrrole, imidazole, oxazole, thiazole, pyrazole and pyrimidine rings and, even though not an aromatic ring, Ar can also represent a cyclohexane ring. The linkages to the aromatic ring can be in the 2,3, 2,4 or 2,5 positions on a five membered ring or in the o, m or p- positions on a six member ring. The $C_6H_{10}$ (cyclohexylene) moiety can be linked in the 1,2, 1,3 and 1,4 positions. The (CH2)x moiety is meant to represent any alkylene moiety including both straight or branched chain forms having a 2:1 hydrogen to carbon ratio. The term alkyl, or the alkyl portions of the aralkyl and alkaryl groups can contain from 1 to 10 carbon atoms and be either straight or branch chained. $R^2$ and $R^3$ are any suitable groups which can be attached to the polysiloxane copolymer backbone for any desired purpose but which does not interfere with the functionality of the resulting product. For example, a hydrosilyl (Si-H) moiety unreacted following coupling of the cyclodextrin to the Si-H groups on the polysiloxane backbone may be reacted with an alkene, such as 1-octene, to cap or deactivate the Si-H group. In that instance $R^2$ would be octyl. Also, crosslinking agents such as tolyl or octyl groups may be attached to the polymer backbone to assist in attaching the polymer to a fused silica capillary tube for use in GC or SFC separations. In such instances $R^3$ may be represented by tolyl or octyl groups. $R^2$ and $R^3$ members selected from the group consisting of alkyl, aralkyl and alkaryl. Representative of preferred $R^2$ and $R^3$ groups are methyl, octyl, phenyl and tolyl.

In Formula I the cyclodextrin is a cycloglucoseoligosaccharide consisting of a cyclo-hexaglucose, (α-cyclodextrin) where n=5 and m=12, cyclo-heptaglucose (β-cyclodextrin) where n=6 and m=14 or cyclo-octaglucose (τ-cyclodextrin) where n=7 and m=16. The $Q_pCH_2CH_2$ spacer group is attached to the glucose via the 6 position on the small rim of the cyclodextrin.

The cyclodextrin polysiloxanes of Formula II have the following general formula (Formula II):

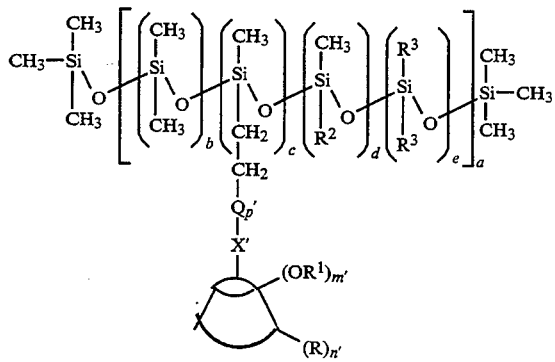

wherein where n' is an integer of 6 to 8, m' is an integer of 11 to 15, X' is a member selected from the group consisting of O, S and NH and Q' is a member selected from the group consisting of $CH_2(CH_2)_x$, $(CH_2)_x$—$XCH_2$, $(CH_2)_x$—$C(O)XCH_2$, $C(O)(CH_2)_x$—$XCH_2$, Ar—$XCH_2$, $(CH_2)_x$—Ar—$XCH_2$, Ar—$(CH_2)_x$—$XCH_2$, $(CH_2)_x$—Ar—$(CH_2)_x$—$XCH_2$, Ar—$C(O)XCH_2$, $(CH_2)_x$—Ar—$C(O)XCH_2$, Ar—$(CH_2)_x$—$C(O)XCH_2$, $(CH_2)_x$—Ar—$(CH_2)_x$—$C(O)XCH_2$, $C(O)$—Ar—$XCH_2$, $C(O)$—$(CH_2)_x$—Ar—$XCH_2$, $C(O)$—Ar—$(CH_2)_x$—$XCH_2$ and $C(O)$—$(CH_2)_x$—Ar—$(CH_2)_2$—$XCH_2$. Otherwise, the meanings given above for Formula I apply. The difference between the two polymers of Formula I and II is in the point of attachment to the cyclodextrin rim. In Formula II the Q' linking moiety is attached at the 2 or 3 positions on the large rim of the cyclodextrin whereas in Formula I the Q moiety is attached at the 6 position of the small rim of the cyclodextrin.

Therefore, in Formula II the cyclodextrin is a cycloglucoseoligosaccharide consisting of a cyclo-hexaglucose, (α-cyclodextrin) where n=6 and m=11, cyclo-heptaglucose (β-cyclodextrin) where n=7 and m=13 or cyclo-octaglucose (T-cyclodextrin) where n=8 and m=15. The $Q'_pCH_2CH_2$ spacer group is attached to the glucose via the 2 or 3 position. The 3 position is not as easily functionalized as is the 2 position.

In both Formulas I and II the preferable cycloglucoseoligosaccharide is a β-cyclodexrin. Also preferred are the embodiments wherein X or X' is O. However in cases where —XC(O)— occurs, X may be preferably NH or O, i.e. an amide or ester linkage. Ar is preferably a phenylene group. x is preferably a numeral of 1–5 and alkyl preferably refers to a group having 1–5 carbon atoms.

Synthesis of 6-Position Functionalized Cyclodextrin Monomers

The preferred procedures to prepare the cyclodextrin polysiloxane polymers in accordance with Formula I are outlined in the description and examples which follow.

The starting material is heptakis(2,3-di-O-methyl)-β-cyclodextrin prepared according to the method disclosed by Yi, et al. *J. Org. Chem.* 1993,58,2651. The starting material is reacted with tosyl chloride to produce the monotosyl-substituted cyclodextrin.

The peralkyl-, monoalkenyl-substituted β-cyclodextrins were prepared from a monotosyl-substituted cyclodextrin. The cyclodextrins were prepared to have arms of various lengths and compositions to serve as models to illustrate the effect of the spacer arm on the enantiomeric separations of solute test molecules. Distinctly different substituents at the remaining 6-positions of cyclodextrin are indicative of the effect that different substituents on the cyclodextrin rims have on the mechanism of enantioselectivity. Results of the chromatographic separations are given in the examples and in the drawings.

Cyclodextrin monofunctionalized at the 6-position has been prepared previously as shown by Melton, et al., *Carbohyd. Res.* 1971, 18, 29; Gibson, et al., *Can. J. Chem.* 1974, 52, 3905; Matsui, et al., *Bull. Chem. Soc. Jpn.* 1978, 51, 3030 and Parrot-Lopez, et al., *Tetrahedron Lett.* 1992, 33, 209.

In the following examples, proton and carbon NMR spectra were recorded at 200 MHz. Heptakis(2,3-di-O-methyl)-β-cyclodextrin was prepared as reported by Yi, et al. *J. Org. Chem.* 1993, 58, 2651. Periodinane was prepared as reported by Dess, et al., *J. Org. Chem.* 1983, 48, 4156.

EXAMPLE 1

Heptakis (2,3-di-O-methyl)-6-O-(p-toluenesulfonyl)-β-cyclodextrin

The pivotal step is the reaction of cyclodextrin with toluenesulfonyl (tosyl) chloride in pyridine to produce the monotosyl-substituted cyclodextrin. Mono (6-O-tosyl)heptakis (2,3-di-O-methyl)-β-cyclodextrin was obtained in a 31% yield from heptakis(2,3-di-O-methyl)-β-cyclodextrin in a manner similar to that reported by Yi et al., supra, for the di(6-O-tosyl) analog. In this Example a solution of tosyl chloride (1.56 g, 8.2 mmol) in 30 mL of dry pyridine was added dropwise to a solution of 14.9 g (11.2 mmol) of heptakis(2,3-di-O-methyl)-β-cyclodextrin (1) in 120 mL of dry pyridine cooled to 5° C. or below. After stirring overnight at room temperature, the mixture was evaporated under reduced pressure at 40° C. to dryness. The residue was dissolved in CHCl$_3$, and the solution was washed with water, cold 3% HCl, aqueous NaHCO$_3$, and water, and then dried (MgSO$_4$). The solid produced from evaporating the solvents was subjected to column chromatography on silica gel (CHCl$_3$:CH$_3$OH/15:1, then 8:1) to give 5.07 g (31% yield) of heptakis(2,3-di-O-methyl)-6-O-(p-toluene sulfonyl)-$\beta$-cyclodextrin (2); mp 156.5°–158° C.; $[\alpha]_D^{25}=132.2°$ (c 3.28, CHCl$_3$); $^1$H NMR $\delta$ 7.81 (d, J=6.8 Hz, 2H), 7.40 (d, J=6.8 Hz, 2H), 5.24–4.98 (m, 7H), 4.45 (d, J=7.3 Hz, 2H), 4.28 (s, 6H, OH), 4.09–3.30 (m, 75 H), 3.27–2.96 (m, 7H), 2.46 (s, 3H); $^{13}$C NMR $\delta$ 145.5, 133.4, 130.3,128.6, 99.2, 98.9, 98.7, 98.5, 82.6, 82.5, 82.4, 82.3, 82.1, 80.5, 72.7, 72.6, 62.0, 61.8, 61.5, 59.2, 59.0, 58.8, 22.1. Anal. Calcd for C$_{63}$H$_{104}$O$_{37}$S: C, 50.94; H, 7.06. Found: C, 51.07; H, 7.18.

The tosyl group of the cyclodextrin of Example 1 was then replaced by a variety of nucleophiles according to the procedures of the following examples.

EXAMPLE 2

6-O-(p-Allyloxyphenyl)heptakis(2,3-di-O-methyl)-$\beta$-cyclodextrin

The reaction of heptakis(2,3-di-O-methyl)-6-O-(p-toluenesulfonyl)-$\beta$-cyclodextrin from Example 1 with sodium p-allyloxyphenoxide in DMF gave the intermediate cyclodextrin 6-O-p-allyloxyphenylheptakis(2,3-di-O-methyl)-$\beta$-cyclodextrin in a yield of 77% as follows. A mixture of p-allyloxyphenol (3.1 g, 20.5 mmol) and NaH (0.49 g, 20.5 mmol) in 100 mL of anhydrous THF was refluxed for 30 min, and then concentrated. A solution of the residue and heptakis(2,3-di-O-methyl)-6-O-(p-toluenesulfonyl)-$\beta$-cyclodextrin (5.1 g, 3.4 mmol) in 100 mL of dry DMF was stirred for 24 h at room temperature, and then concentrated. The residue was partitioned between CHCl$_3$ and water. The organic layer was separated, dried and concentrated. The crude product was subjected to column chromatography on silica gel (CHCl$_3$:CH$_3$OH/15:1) to give 6-O-p-allyloxyphenylheptakis(2,3-di-O-methyl)-$\beta$-cyclodextrin(3.68 g, 74% yield); mp 156°–158° C.; $[\alpha]_D^{25}+142.1°$ (c 1.83, CHCl$_3$); $^1$H NMR $\delta$ 6.92–6.75 (m, 4H), 6.05 (m, 1H), 5.37 (m, 2H), 5.04 (m, 7H), 4.46 (d, J=5.2 Hz, 2H), 4.32 (s, 6H, OH), 4.07–3.02 (m, 84H); $^{13}$C NMR $\delta$ 153.4, 153.3, 134.1, 117.8, 116.4, 116.0, 99.6, 99.2, 99.0, 98.3, 82.4, 82.0, 81.6, 81.5, 81.4, 81.0, 80.7, 80.5, 80.4, 80.3, 79.0, 72.7, 72.6, 72.4, 72.3, 72.1, 71.1, 71.0, 69.8, 69.6, 62.0, 61.8, 61.7, 61.5, 61.3, 61.2, 61.1, 59.4. Anal. Calcd for C$_{65}$H$_{106}$O$_{36}$C, 53.34; H, 7.30. Found: C, 53.23; H, 7.43.

The intermediate of Example 2 was converted into other $\beta$-cyclodextrin derivatives with different substituents at the other 6-O positions as shown in Examples 3, 4 and 5.

EXAMPLE 3

6$^A$-O-(p-Allyloxyphenyl)heptakis(2,3-di-O-methyl)-6$^B$,6$^C$,6$^D$,6$^E$,6$^F$,6$^G$-hexa-O-methyl-$\beta$-cyclodextrin Methylation of 6-O-p-allyloxyphenylheptakis(2,3-di-O-methyl)-$\beta$-cyclodextrin prepared as in Example 2 with sodium hydride and iodomethane in DMF gave permethylated 6-O-p-allyloxyphenyl-$\beta$-cyclodextrin as follows.

A solution of 6-O-p-allyloxyphenylheptakis(2,3-di-O-methyl)-$\beta$-cyclodextrin (3.1 g, 2.1 mmol) in 50 mL of DMF was treated with NaH (3.0 g, 126 mmol) at room temperature for 2 h. The mixture was cooled to 0° C. and 21.4 g (151 mmol) of CH$_3$I was added. The mixture was stirred at 0° C. for 2 h, at room temperature for 24 h and CH$_3$OH was added to decompose the excess NaH. The reaction mixture was evaporated to dryness and the residue was partitioned between CHCl$_3$ and water. The organic phase was separated, washed successively with water, aqueous Na$_2$S$_2$O$_3$, and water, and then dried and concentrated. Column chromatography on silica gel CHCl$_3$:CH$_3$OH/80:1) of the crude product gave 6$^A$-O-(p-Allyloxyphenyl)heptakis(2,3-di-O-methyl)-6$^B$,6$^C$,6$^D$,6$^E$,6$^F$,6$^G$-hexa-O-methyl-$\beta$-cyclodextrin (1.76 g, 54% yield); mp 220°–222° C.; $[\alpha]_D^{25}+150.1°$ (c 2.50, CHCl$_3$); $^1$H NMR $\delta$ 6.87–6.71 (m, 4H), 5.99 (m, 1H), 5.28 (m, 2H), 5.15–4.98 (m, 7H), 4.42 (d, J=5.19 Hz, 2H), 4.28–3.00 (m, 102H); $^{13}$C NMR $\delta$ 153.6, 153.4, 133.9, 117.8, 115.9, 99.8, 99.4, 99.3, 82.5, 82.4, 82.2, 81.2, 80.9, 80.8, 80.7, 71.9, 71.7, 71.4, 70.9, 69.8, 62.0, 61.9, 59.4, 59.3, 59.1, 59.0, 58.9, 58.7. Anal. Calcd for C$_{72}$H$_{118}$O$_{36}$: C, 55.06; H, 7.75. Found: C, 55.03; H, 7.68.

EXAMPLE 4

6$^A$-O-(p-Allyloxyphenyl)heptakis(2,3-di-O-methyl)-6$^B$,6$^C$,6$^D$,6$^E$,6$^G$-hexa-O-acetyl-$\beta$-cyclodextrin Acetylation of 6-O-p-allyloxyphenylheptakis(2,3-di-O-methyl)-$\beta$-cyclodextrin prepared as in Example 2 with acetic anhydride in pyridine gave the hexaacetate ester 6$^A$-O-(p-Allyloxyphenyl)heptakis (2,3-di-O-methyl)-6$^B$,6$^C$,6$^D$,6$^E$,6$^F$,6$^G$-hexa-O-acetyl-$\beta$-cyclodextrin as follows.

A solution of 6-O-p-allyloxyphenylheptakis(2,3-di-O-methyl)-$\beta$-cyclodextrin (0.24 g, 0.16 mmol) in 10 mL of acetic anhydride and 10 mL of pyridine was stirred at 100° C. for 4 h, and then concentrated. Column chromatography (CHCl$_3$:CH$_3$OH/80:1) of the residue produced amorphous 6$^A$-O-(p-Allyloxyphenyl)heptakis (2,3-di-O-methyl)-6$^B$,6$^C$,6$^D$,6$^E$,6$^F$,6$^G$-hexa-O-acetyl-$\beta$-cyclodextrin (0.26 g, 93% yield); mp 102°–104° C.; $[\alpha]_D^{25}+130.6°$ (c 0.96, CHCl$_3$); $^1$H NMR $\delta$ 6.93–6.75 (m, 4H), 6.04 (m, 1H), 5.34 (m, 2H), 5.18–4.98 (m, 7H), 4.63–4.38 (m, 8H), 4.38–4.03 (m, 7H), 4.03–3.76 (m, 7H), 3.76–3.30 (m, 57H), 3.30–3.04 (m, 7H), 2.20–1.98 (m, 18H); $^{13}$C NMR $\delta$ 171.0, 170.9, 153.5, 153.2, 134.1, 117.8, 116.3, 116.1, 100.2, 99.6, 98.7, 82.6, 82.4, 82.2, 82.0, 81.8, 81.7, 81.6, 81.3, 80.9, 71.3, 70.2, 70.1, 69.8, 69.6, 67.5, 64.0, 63.8, 62.2, 62.0, 61.9, 61.8, 59.6, 59.5, 59.2, 58.8, 21.3. Anal. Calcd for C$_{77}$H$_{118}$O$_{42}$: C, 53.90; H, 6.93. Found: C, 53.78; H, 7.06.

EXAMPLE 5

6$^A$-O-(p-Allyloxyphenyl)heptakis(2,3-di-O-methyl)-6$^B$,6$^C$,6$^D$,6$^E$,6$^F$,6$^G$-hexa-O-methanesulfonyl-$\beta$-cyclodextrin Treatment of 6-O-p-allyloxyphenylheptakis(2,3-di-O-methyl)-$\beta$-cyclodextrin prepared as in Example 2 with methanesulfonyl (mesyl) chloride in pyridine produced hexamesylate ester b$^A$-O-(p-Allyloxyphenyl)heptakis(2,3-di-O-methyl)-6$^B$,6$^C$,6$^D$,6$^E$,6$^F$,6$^G$-hexa-O-methanesulfonyl-$\beta$-cyclodextrin in a 74% yield as follows.

A solution of 6-O-p-allyloxyphenylheptakis(2,3-di-O-methyl)-$\beta$-cyclodextrin (2.0 g, 1.36 mmol) in 20 mL of dry pyridine was cooled to −10° C., treated with CH$_3$SO$_2$Cl (1.9 g, 16.3 mmol), and kept overnight at 5° C. The mixture was poured into 100 mL of icewater, the precipitate was filtered, washed with cold water, and dissolved in CHCl$_3$. The solution was washed with water, dried and concentrated. The residue was subjected to column chromatography (C$_6$H$_6$:C$_2$H$_5$OH/40:1, then 30:1) to produce 6$^A$-O-(p-Allyloxyphenyl)heptakis(2,3-di-O-methyl)-6$^B$,6$^C$,6$^D$,6$^E$,6$^F$,6$^G$-hexa-O-methanesulfonyl-β-cyclodextrin (1.95 g, 74% yield); mp 134°–135° C.; [α]$_D^{25}$+112.8° (c 0.88, CHCl$_3$); $^1$H NMR δ 6.92–6.77 (m, 4H), 6.02 (m, 1H), 5.31 (m, 2H), 5.16–5.00 (m, 7H), 4.73–3.38 (m, 79H), 3.31–3.12 (m, 7H), 3.08 (s, 18H); $^{13}$C NMR δ 153.5, 153.3, 134.1, 117.9, 116.2,115.9, 99.5, 99.3, 98.3, 82.2, 82.1, 81.9, 81.8, 81.6, 81.0, 80.7, 80.2, 79.5, 70.9, 70.1, 69.8, 69.6, 67.8, 62.1, 61.9, 61.8, 61.6, 59.8, 59.7, 59.3, 59.2, 59.0, 37.7, 37.6, 37.3. Anal. Calcd for C$_{71}$H$_{118}$O$_{48}$S$_6$: C, 44.14; H, 6.16. Found: C, 44.26; H, 6.30.

EXAMPLE 6

6$^A$-O-(p-Allyloxyphenyl)heptakis(2,3-di-O-methyl)-6$^B$,6$^C$,6$^D$,6$^E$,6$^F$,6$^G$-hexadeoxy-6$^B$,6$^C$,6$^D$,6$^E$,6$^F$,6$^G$-hexaiodo-β-cyclodextrin The mesyl groups of the cyclodextrin formed in Example 5 were replaced by the iodide anion in DMF to produce the hexaiodo-βcyclodextrin derivative in the following manner.

A solution of 6$^A$-O-(p-Allyloxyphenyl)heptakis(2,3-di-O-methyl)-6$^B$,6$^C$,6$^D$,6$^E$,6$^F$,6$^G$-hexa-O-methanesulfonyl-β-cyclodextrin (1.86 g, 0.96 mmol) in 50 mL of DMF was stirred with NaI (2.34 g, 15.6 mmol) at 100° C. for 3 h. The mixture was concentrated. The residue was partitioned between CHCl$_3$ and water. The organic layer was separated, washed with water, dried and concentrated. Column chromatography (silica gel) (C$_6$H$_6$:C$_2$H$_5$OH/30:1) of the product gave 6$^A$-O-(p-Allyloxyphenyl)heptakis(2,3-di-O-methyl)-6$^B$,6$^C$,6$^D$,6$^E$,6$^F$,6$^G$-hexadeoxy- 6$^B$,6$^C$,6$^D$,6$^E$,6$^F$,6$^G$-hexaiodo-β-cyclodextrin (1.68 g, yield 82%); mp 128°–130° C.; [α]$_D^{25}$+89.2° (c 1.14, CHCl$_3$); $^1$H NMR δ 6.92–6.78 (m, 4H), 6.03 (m, 1H), 5.46–5.00 (m, 9H), 4.48 (m, 2H), 4.27–3.04 (m, 84H); $^{13}$C NMR δ 153.6, 153.2, 134.1, 117.9, 116.3, 116.1, 99.7, 98.7, 98.5, 84.9, 84.7, 84.3, 84.0, 82.3, 82.1, 82.0, 81.9, 81.8, 71.4, 70.9, 70.7, 70.4, 69.9, 62.1, 61.9, 59.5, 59.4, 59.3, 59.2, 59.1, 10.2. Anal. Calcd for C$_{65}$H$_{100}$O$_{30}$I$_6$: C, 36.78; H, 4.75. Found: C, 36.89; H, 4.62.

EXAMPLE 7

6$^A$-O-(Allyloxyphenyl)heptakis(2,3-di-O-methyl)-6$^B$,6$^C$,6$^D$,6$^E$,6$^F$,6$^G$-hexadeoxy-β-cyclodextrin The hexaiodocyclodextrin of Example 6 was next transformed into 6$^A$-O-p-allyloxyphenylheptakis(2,3-di-O-methyl)-6$^B$,6$^C$,6$^D$,6$^E$,6$^F$,6$^G$-hexadeoxy-β-cyclodextrin by reduction with sodium borohydride in DMF as follows.

A solution of 6$^A$-O-(p-Allyloxyphenyl)heptakis(2,3-di-O-methyl)-6$^B$,6$^C$,6$^D$,6$^E$,6$^F$,6$^G$-hexadeoxy-6$^B$,6$^C$,6$^D$,6$^E$,6$^F$,6$^G$-hexaiodo-β-cyclodextrin (280 mg, 0.13 mmol) in 10 mL of DMF was stirred with NaBH$_4$ at 70° C. for 2 h and evaporated to dryness under reduced pressure. The solution of the residue in 150 mL of CHCl$_3$ was washed twice with water, dried and concentrated. Column chromatography (silica gel) (C$_6$H$_{14}$:CH$_3$CO$_2$C$_2$H$_5$:C$_2$H$_5$OH/40:10:1) of the crude product gave 6$^A$-O-(p-Allyloxyphenyl)heptakis(2,3-di-O-methyl)-6$^B$,6$^C$,6$^D$,6$^E$,6$^F$,6$^G$-hexadeoxy-β-cyclodextrin (0.11 g, 61% yield); mp 104°–106° C.; [α]$_D^{25}$+135.1° (c 0.87, CHCl$_3$); $^1$H NMR δ 6.89– 6.78 (m, 4H), 6.03 (m, 1H), 5.32 (m, 2H), 5.11 (d, J=3.1 Hz, 1H), 5.08–4.89 (m, 6H), 4.46 (m, 2H), 4.38–3.34 (m, 59H), 3.34–2.95 (m, 13H), 1.60–1.13 (m, 18H); $^{13}$C NMR δ 153.4, 134.0, 117.9, 116.0, 115.9, 99.6, 99.3, 99.0, 87.6, 87.5, 87.2, 87.1, 87.0, 83.0, 82.9, 82.8, 82.5, 82.4, 82.1, 81.0, 77.7, 70.9, 69.8, 69.6, 68.1, 67.6, 67.5, 62.1, 61.9, 61.8, 61.7, 59.1, 59.0, 58.9, 18.8, 18.6. Anal. Calcd for C$_{65}$H$_{106}$O$_{30}$: C, 57.09; H, 7.81. Found: C, 56.99; H, 7.80.

The above syntheses show the preparation of monosubstituted β-cyclodextrins with O-methyl, O-acetyl, O-mesyl or deoxy units in the other 6-positions. This multiplicity of 6-position substitutions demonstrate that some variability in substituents at the 6-position does not materially affect the ability of the corresponding phases to separate enantiomers.

EXAMPLE 8

Heptakis(2,3-di-O-methyl)-6$^B$,6$^C$,6$^D$,6$^E$,6$^F$,6$^G$-hexa-O-methyl-6$^A$-O-toluenesulfonyl-β-cyclodextrin The monotosylate cyclodextrin ester of Example 1 was methylated under mild conditions using methyl trifluoromethanesulfonate and 2,6-tert-butyl-4-methylpyridine in dichloromethane to give the permethylated monotosyl-β-cyclodextrin heptakis(2,3-di-O-methyl)-6$^B$,6$^C$,6$^D$,6$^E$,6$^F$,6$^G$-hexa-O-methyl-6$^A$-O-toluenesulfonyl-β-cyclodextrin in a 93% yield as follows.

A mixture of heptakis(2,3-di-O-methyl)-6-O-(p-toluenesulfonyl)-β-cyclodextrin (0.22 g, 0.15 mmol), methyl triflate (0.15 mL, 1.33 mmol) and 2,6-di-(tert-butyl)-4-methylpyridine (0.37 g, 1.80 mmol) in 6 mL of CH$_2$Cl$_2$ was heated in a sealed tube for 2.5 h at 80° C. and cooled. CH$_3$OH (2 mL) was added, and the mixture was kept for 30 min at rt, and concentrated. A solution of the residue in CHCl$_3$ was washed successively with water, cold 3% HCl, aqueous NaHCO$_3$, and water, and then dried and concentrated. The product was subjected to column chromatography on silica gel (CHCl$_3$:CH$_3$OH/100:1) to produce heptakis(2,3-di-O-methyl)-6$^B$,6$^C$,6$^D$,6$^E$,6$^F$,6$^G$-hexa-O-methyl-6$^A$-O-toluenesulfonyl-β-cyclodextrin (0.43 g, 93% yield); mp 98°–100° C.; [α]$_D^{25}$+131.9° (c 2.22, CHCl$_3$); $^1$H NMR δ 7.74 (d, J=6.8 Hz, 2H), 7.35 (d, J=6.8 Hz, 2H), 5.21–4.92 (m, 7H), 4.45 (d, J=7.3 Hz, 2H), 4.17–3.26 (m, 93H), 3.26–2.95 (m, 7H), 2.43 (s, 3H); $^{13}$C NMR δ 145.2, 133.8, 130.3, 128.4, 99.7, 99.6, 99.6, 99.1, 98.8, 82.7, 82.6, 82.4, 82.1, 81.0, 80.8, 80.1, 79.9, 71.7, 71.6, 71.4, 71.1, 69.9, 62.1, 62.0, 61.9, 61.7, 59.6, 59.4, 59.3, 59.0, 58.8, 58.7, 58.5, 22.1. Anal. Calcd for C$_{69}$H$_{116}$O$_{37}$S: C, 52.80; H, 7.45. Found: C, 53.06; H, 7.72.

EXAMPLE 9

6$^A$-Allyl-6$^A$-deoxyheptakis(2,3-di-O-methyl)-6$^B$,6$^C$,6$^D$,6$^E$,6$^F$,6$^G$-hexa-O-methyl-βcyclodextrin A coupling reaction of the cyclodextrin of Example 8 with freshly prepared allylmagnesium bromide in the presence of dilithiumtetrachlorocuprate produced 6$^A$-Allyl-6$^A$-deoxyheptakis(2,3-di-O-methyl)-6$^B$,6$^C$,6$^D$,6$^E$,6$^F$,6$^G$-hexa-O-methyl-βcyclodextrin, i.e. a permethylated monoallyl-β-cyclodextrin with a nonoxy spacer as follows.

A solution of 0.47 g (0.30 mmol) of heptakis(2,3-di-O-methyl)-6$^B$,6$^C$,6$^D$,6$^E$,6$^F$,6$^G$-hexa-O-methyl-6$^A$-O-toluenesulfonyl-β-cyclodextrin in 10 mL of dry benzene was slowly added to 10 mL of a stirred 1.0 M ethereal solution of allyl-MgBr (freshly prepared) at 0° C. under an argon atmosphere. Li$_2$CuCl$_4$ (3 mL in THF) was added and the reaction mixture was stirred for 30 min at 0° C. and for 22 h at room temperature. Saturated aqueous NH$_4$Cl solution (20 mL) was added at 0° C. to decompose the excess Grignard reagent. The mixture was diluted with CHCl$_3$, and organic layer was separated and washed with water, and then dried and concentrated. The residue was purified by column chromatography on silica gel (CH$_3$OH: CHCl$_3$/80:1) to give 6$^A$-allyl-6$^A$-deoxyheptakis (2,3 -di-O-methyl)-6$^B$,6$^C$,6$^D$,6$^E$,6$^F$,6$^G$-hexa-O-methyl-$\beta$-cyclodextrin (0.24 g, 55% yield); mp 75°–77° C.; [$\alpha$]$_D^{25}$+140.7° (c 1.10, CHCl$_3$); $^1$H NMR $\delta$ 5.83 (m, 1H), 5.23–4.90 (m, 9H), 4.06–3.29 (m, 93H), 3.18 (dd, J$_1$=6.7 Hz, J$_2$=3.2 Hz, 7H), 2.05 (m, 2H), 1.60 (m, 2H); $^{13}$C NMR $\delta$ 139.0, 115.0, 99.8, 99.4, 99.3, 99.2, 98.6, 83.7, 83.2, 82.4, 82.3, 82.1, 81.2, 80.8, 80.6, 79.9, 71.9, 71.8, 71.7, 71.6, 71.5, 71.4, 71.2, 70.8, 62.2, 62.1, 62.0, 61.9, 61.7, 61.5, 59.7, 59.5, 59.4, 59.2, 59.1, 59.0, 58.9, 58.7, 58.6, 31.7, 30.0. Anal. Calcd for C$_{65}$H$_{114}$O$_{34}$: C, 54.53; H, 8.04. Found: C, 54.38; H, 7.79.

EXAMPLE 10

6$^A$-O-Allylheptakis(2,3-di-O-methyl)-6$^B$,6$^C$,6$^D$,6$^E$,6$^F$,6$^G$-hexa-O-methyl-$\beta$-cyclodextrin Nucleophilic substitution of the tosylate group of the permethylated monotosyl-$\beta$-cyclodextrin of Example 8 with sodium allyloxide in DMF gave a permethylated monoallyl-$\beta$-cyclodextrin as follows.

A solution of allyl alcohol (0.29 g, 5.0 mmol) in 20 mL of DMF was treated with NaH (96 mg, 4 mmol) for 4 h at rt. The permethylated monotosyl-$\beta$-cyclodextrin of Example 8 (0.31 g 0.2 mmol) was added at 0° C. and the mixture was stirred for 24 h at room temperature. CH$_3$I was added to decompose the excess allyloxide at 0° C. and the mixture was concentrated. A solution of the residue in CHCl$_3$ was washed twice with water, dried and concentrated. Column chromatography (silica gel) (CHCl$_3$:CH$_3$OH/40:1) of the product gave 6$^A$-O-allylheptakis(2,3-di-O-methyl)-6$^B$,6$^C$,6$^D$,6$^E$,6$^F$,6$^G$-hexa-O-methyl-$\beta$-cyclodextrin (0.20 g, 69% yield); mp 86°–88° C.; [$\alpha$]$_D^{25}$+138.6° (c 0.90, CHCl$_3$); $^1$H NMR $\delta$ 5.83 (m, 1H), 5.12 (m, 2H), 5.05 (d, J=3.1 Hz, 7H), 3.96 (d, J=4.1 Hz, 2H), 3.84–3.23 (m, 95H), 3.10 (dd, J$_1$=6.8 Hz, J$_2$=3.1 Hz, 7H); $^{13}$C NMR $\delta$ 135.6, 117.0, 99.7, 82.5, 82.2, 80.9, 80.8, 72.5, 71.8, 71.5, 71.3, 69.4, 61.8, 59.3, 58.9, 58.8. Anal. Calcd for C$_{65}$H$_{114}$O$_{35}$: C, 53.64; H, 7.89. Found: C, 53.55; H, 7.91.

EXAMPLE 11

Heptakis (2,3-di-O-methyl)-6$^B$,6$^C$,6$^D$,6$^E$,6$^F$,6$^G$-hexa-O-methyl-6$^A$-O-($\omega$-undecylenyl)-$\beta$cyclodextrin Nucleophilic substitution of the tosylate group of the permethylated monotosyl-$\beta$-cyclodextrin of Example 8 with sodium $\omega$-undecylenyloxide in DMF gave a permethylated mono-$\omega$-undecyleny-$\beta$-cyclodextrins as follows.

The procedure of Example 10 was followed using 0.82 g (4.8 mmol) of $\omega$-undecenyl alcohol, 0.12 g (4.8 mmol) of NaH and 0.37 g (0.24 mmol) of the permethylated monotosyl-$\beta$-cyclodextrin of Example 8 to give 0.19 g (50% yield) of heptakis (2,3-di-O-methyl)-6$^B$,6$^C$,6$^D$,6$^E$,6$^F$,6$^G$-hexa-O-methyl-6$^A$-O-($\omega$-undecylenyl) -$\beta$-cyclodextrin; mp 77°–79° C.; [$\alpha$]$_D^{125}$+135.7° (c 1.30, CHCl$_3$); $^1$H NMR $\delta$ 5.74 (m, 1H), 5.08 (d, J=3.1 Hz, 7H), 4.91 (m, 2H), 3.90–3.25 (m, 97H), 3.13 (dd, J$_1$=6.8 Hz, J$_2$=3.1 Hz, 7H), 1.98 (m, 2H), 1.52 (m, 2H), 1.22 (m, 12H); $^{13}$C NMR $\delta$ 139.5, 114.6, 99.4, 99.2, 82.6, 82.4, 82.2, 81.1, 80.9, 80.8, 80.6, 71.9, 71.7, 71.4, 61.9, 59.4, 59.0, 58.9, 34.2, 30.2, 30.1, 30.0, 29.9, 29.5, 29.3, 26.7. Anal. Calcd for C$_{73}$H$_{130}$O$_{35}$: C, 55.92; H, 8.36. Found: C, 56.17; H, 8.43.

The alkene-substituted cyclodextrins of Example 9–11 provide a means to study cyclodextrin phases that have a short non-aromatic ring-containing tether (Example 9 and 10) to a polysiloxane and one that has a long chain aliphatic tether (Example 11).

Examples 12–16 illustrate the stepwise preparation of a permethylated 6-deoxy-6-methylene-$\beta$-cyclodextrin starting from heptakis(2,3-di-O-methyl)-$\beta$-cyclodextrin.

EXAMPLE 12

6-O-(tert-Butyldimethylsilyl)heptakis(2,3-di-O-methyl)-$\beta$-cyclodextrin

Heptakis(2,3-di-O-methyl)-$\beta$-cyclodextrin was treated with tert-butyldimethylsilyl chloride and imidazole in DMF to produce 6-O-(tert-butyldimethylsilyl) heptakis(2,3-di-O-methyl)-$\beta$-cyclodextrin as follows.

To a stirred mixture of dried heptakis(2,3-di-O-methyl)-$\beta$-cyclodextrin (8.9 g, 6.7 mmol) and imidazole (0.82 g, 12.1 mmol) in 100 mL of dry DMF, was added, dropwise during 30 min at room temperature, a solution of tert-butyldimethylsilyl chloride (1.5 g, 10.5 mmol) in 30 mL of dry DMF. The mixture was stirred for 3 h at room temperature and concentrated. A solution of the residue in CHCl$_3$ was washed successively with water, cold 3% HCl, aqueous NaHCO$_3$, and water, and then dried and concentrated. Column chromatography on silica gel (CHCl$_3$:CH$_3$OH/15:1) of the product gave 6-O-(tert-butyldimethylsilyl)heptakis(2,3-di-O-methyl)-$\beta$-cyclodextrin (3.22 g, 33% yield); mp 149°–150° C.; [$\alpha$]$_D^{25}$+138.1° (c 1.24, CHCl$_3$); $^1$H NMR $\delta$ 5.29–4.94 (m, 7H), 4.60 (broad s, 6H, OH), 4.20–3.28 (m, 77H), 3.28–3.00 (m, 7H), 0.86 (s, 9H), 0.03 (s, 6 H); $^{13}$C NMR $\delta$ 99.3, 98.8, 98.7, 82.8, 82.7, 82.5, 82.4, 82.3, 82.2, 82.1, 82.0, 81.9, 81.8, 81.4, 81.1, 81.0, 78.4, 73.1, 72.8, 72.7, 72.4, 72.3, 62.5, 62.3, 62.2, 62.0, 61.9, 61.8, 61.6, 61.4, 61.3, 59.6, 59.0, 58.8, 58.3, 26.4, 18.8, −4.6, −4.7. Anal. Calcd for C$_{62}$H$_{112}$O$_{35}$Si: 51.51; H, 7.81. Found: C, 51.39; H, 7.64.

EXAMPLE 13

6$^A$-O-(tert-Butyldimethylsilyl)heptakis(2,3-di-O-methyl)-6$^B$,6$^C$,6$^D$,6$^E$,6$^F$,6$^G$-hexa-O-methyl-$\beta$-cyclodextrin The cyclodextrin obtained in Example 12 was methylated to give permethylated 6-O-(tert-butyldimethylsilyl)-$\beta$-cyclodextrin as follows.

A solution of 6-O-(tert-butyldimethylsilyl)heptakis (2,3 -di-O-methyl)-$\beta$-cyclodextrin (0.66 g, 0.46 mmol) in 20 mL of DMF was treated with NaH (0.79 g, 32.9 mmol), followed by adding CH$_3$I (5.60 g, 39.5 mmol). The mixture was stirred for 24 h at rt. CH$_3$OH was added at 0° C. to decompose the excess NaH, and the mixture was concentrated. The residue was partitioned between CHCl$_3$ and water. The organic layer was separated, washed with aqueous Na$_2$S$_2$O$_3$ and water, and then dried and concentrated. The crude product was purified by column chromatography (CHCl$_3$:CH$_3$OH/80:1) to give 6$^A$-O-(tert-Butyldimethylsilyl)heptakis(2,3-di-O-methyl)-6$^B$,6$^C$,6$^D$,6$^E$,6$^F$,6$^G$-hexa-O-methyl-$\beta$-cyclodextrin (0.48 g, 69% yield); mp 103°–104° C.; [$\alpha$]$_D^{25}$+130.6° (c 1.09, CHCl$_3$); $^1$H NMR $\delta$ 5.14–4.97 (m, 7H), 4.05–3.24 (m, 95H), 3.10 (dd, J$_1$=6.75 Hz, J$_2$=3.12 Hz, 7H), 0.81 (s, 9H), −0.02 (s, 6H); $^{13}$C NMR $\delta$ 99.6, 99.4, 99.2, 99.0, 98.6, 82.5, 82.3, 82.2, 82.1, 81.1, 81.0, 80.7, 80.6, 80.3, 80.1, 79.7, 72.6, 71.8, 71,3, 61,9, 61.8, 59.4, 59.1, 58.9, 58.8, 26.4, 18.8, −4.6, −4.7. Anal. Calcd for C$_{68}$H$_{124}$O$_{35}$Si: C, 53.39; H, 8.17. Found: C, 53.24; H, 7.92.

EXAMPLE 14

Heptakis(2,3-di-O-methyl)-$6^B,6^C,6^D,6^E,6^F,6^G$-hexa-O-methyl-$\beta$-cyclodextrin The cyclodextrin derivative of Example 13 was deprotected using $NH_4F^{11}$ to form a monohydroxy cyclodextrin as follows.

A solution of $6^A$-O-(tert-Butyldimethylsilyl)heptakis(2,3-di-O-methyl)-$6^B,6^C,6^D,6^E,6^F,6^G$-hexa-O-methyl-$\beta$-cyclodextrin (0.36 g, 0.24 mmol) in 70 mL of $CH_3OH$ was refluxed with $NH_4F$ (104 mg, 2.82 mmol) for 24 h, and then concentrated. The solution of the residue in ethyl acetate was filtered through Celite, and the filtrate was concentrated. Column chromatography ($CHCl_3$: $CH_3OH/80:1$) of the crude product gave heptakis (2,3-di-O-methyl)-$6^B,6^C,6^D,6^E,6^F,6^G$-hexa-O-methyl-$\beta$-cyclodextrin (0.24 g, 73% yield); mp 99°–101° C.; $[\alpha]_D^{25}$ +142.3° (c 1.07, $CHCl_3$); $^1H$ NMR $\delta$ 5.24–4.97 (m, 7H), 4.05–3.29 (m, 95H), 3.15 (dd, $J_1$=6.8 Hz, $J_2$=3.1 Hz, 7H), 2.65 (s, 1H, OH); $^{13}C$ NMR $\delta$ 99.4, 99.3, 82.8, 82.6, 82.5, 82.4, 82.3, 82.2, 82.1, 8.19, 81.6, 81.0, 80.5, 80.3, 79.0, 72.0, 71.9, 71.8, 71.6, 71.5, 71.3, 62.0, 61.9, 61.8, 61.7, 61.5, 59.5, 59.4, 59.1, 58.9, 58.8, 58.7, 58.6. Anal. Calcd for $C_{62}H_{110}O_{35}$: C, 52.61; H, 7.83. Found: C, 52.79; H, 8.00.

EXAMPLE 15

$6^A$-Aldehydoheptakis(2,3-di-O-methyl)-$6^B,6^C,6^D,6^E,6^F,6^G$-hexa-O-methyl-$\beta$-cyclodextrin A methylated aldehydo cyclodextrin derivative was prepared by oxidizing the compound of Example 14 with periodinane.

A solution of heptakis (2,3-di-O-methyl)-$6^B,6^C,6^D,6^E,6^F,6^G$-hexa-O-methyl-$\beta$-cyclodextrin (0.56 g, 0.4 mmol) in 5 mL of $CH_2Cl_2$ was stirred with periodinane (0.50 g, 1.2 mmol) for 2 h at 0° C. and then for 20 h at room temperature. The mixture was diluted with 20 mL of ethyl ether, poured into 20 mL of ice-cold saturated $NaHCO_3$ containing $Na_2S_2O_3$ (2.5 g, 10 mmol), and shaken for 5 min. The organic phase was separated and washed with saturated $NaHCO_3$, water, and brine, and then dried and concentrated. Column chromatography on silica gel ($CHCl_3$:$CH_3OH/80:1$) of the product gave $6^A$-aldehydoheptakis(2,3-di-O-methyl)-$6^B,6^C,6^D,6^E,6^F,6^G$-hexa-O-methyl-$\beta$-cyclodextrin (0.27 g, 48% yield); mp 88°–90° C.; $[\alpha]_D^{25}$+134.0° (c 1.05, $CHCl_3$); $^1H$ NMR $\delta$ 9.69 (d, J=2.1 Hz, 1H), 5.25–5.02 (m, 7H), 4.25 (m, 1H), 3.95–3.02 (m, 99H); $^{13}C$ NMR $\delta$ 198.2, 99.5, 99.4, 99.2, 99.1, 82.6, 82.5, 82.4, 82.2, 81.9, 81.3, 81.2, 81.1, 81.0, 80.7, 80.3, 80.0, 71.9, 71.8, 71.6, 71.5, 71.4, 71.2, 62.1, 62.0, 61.8, 61.3, 59.4, 59.0, 58.9, 58.8. Anal. Calcd for $C_{62}H_{108}O_{35}$: C 52.68; H, 7.70. Found: C, 52.71; H, 7.57.

EXAMPLE 16

$6^A$-Deoxyheptakis(2,3-di-O-methyl)-$6^B,6^C,6^D,6^E,6^F,6^G$-hexa-O-methyl-$6^A$-methylene-$\delta$-cyclodextrin Permethylated 6-deoxy-6-methylene-$\beta$-cyclodextrin was obtained by the reaction of the aldehyde obtained in Example 15 with methyltriphenylphosphonium iodide and phenyllithium in THF in a yield of 64% as follows.

A 100-mL three-necked round-bottomed flask equipped with a pressure-equalizing dropping funnel, thermometer, magnetic stirring bar, and serum caps was charged with 12 1 mg (0.3 mmol) of $(C_6H_5)_3PCH_3I$ and 10 mL of THF, and then was flushed with argon. The flask was cooled in an ice-bath and the suspension was stirred under a positive pressure of argon. About 30 $\mu L$ of 2M (0.06 mmol) $C_6H_5Li$ in 30: 70 ether-cyclohexane was added dropwise until the suspension developed a permanent yellow color. $C_6H_5Li$ (0.12 mL of 2M, 0.24 mmol) was added dropwise over 10 min. The ice bath was removed and the orange suspension containing excess phosphonium salt was stirred at room temperature for 30 min. The reaction mixture was stirred and cooled to 0° C. to 5° C. and a solution of $6^A$-aldehydoheptakis(2,3-di-O-methyl)-$6^B,6^C,6^D,6^E,6^F,6^G$-hexa-O-methyl-$\beta$-cyclodextrin (0.28 g, 0.2 mmol) in 10 mL of THF was added dropwise over 10 min. The dropping funnel was rinsed with a small amount of THF. The mixture was stirred at room temperature for 2 h. The light orange mixture was hydrolyzed by adding 2 mL of $CH_3OH$ and most of the solvent was removed under reduced pressure to give a slurry. The slurry was diluted with 50 mL of ethyl acetate and the suspension was filtered through 5 g of Celite and 5 g of Florisil. The Celite and Florisil were washed with 100 mL of ethyl acetate. Rotary evaporation of the filtrate provided 0.32 g of crude product, which was subjected to column chromatography ($CHCl_3$:$CH_3OH/80:1$) to give $6^A$-deoxyheptakis(2,3-di-O-methyl)-$6^B,6^C,6^D,6^E,6^F,6^G$-hexa-O-methyl-$6^A$-methylene-$\beta$-cyclodextrin (0.18 g, 64% yield); mp 95°–97° C.; $[\alpha]_D^{25}$+140.4° (c, 0.54, $CHCl_3$); $^1H$ NMR $\delta$ 6.08 (m, 1H), 5.49–5.00 (m, 9H), 4.21 (m, 1H), 4.03–3.02 (m, 99H); $^{13}C$ NMR $\delta$ 136.8, 118.6, 99.6, 99.5, 99.4, 99.2, 99.0, 98.7, 83.5, 83.0, 82.6, 82.5, 82.4, 82.3, 82.2, 82.0, 81.9, 81.7, 81.6, 82.5, 81.4, 81.3, 81.2, 80.9, 80.6, 80.0, 72.1, 71.8, 71.6, 71.5, 71.4, 71.2, 71.1, 71.0, 62.3, 62.1, 62.0, 61.7, 61.6, 59.7, 59.4, 59.3, 59.0, 58.8, 58.6. Anal. Calcd for $C_{63}H_{110}O_{34}$: C, 53.61; H, 7.85. Found: C, 53.51; H, 7.97.

The cyclodextrin derivative of this example leads to preparation of a polysiloxane containing permethylated cyclodextrin without an oxygen atom in the tether or linking arm.

Another type or class of permethylated monoalkenyl-$\beta$cyclodextrins which are amenable for preparation in a large scale are those containing an amide bond. Exemplary of these is a permethylated 6-(p-allyloxybenzamido)-6-deoxy-$\beta$-cyclodextrin the preparation of which is described in the following Examples 17 to 19.

EXAMPLE 17

$6^A$-Azido-$6^A$-deoxyheptakis(2,3-di-O-methyl)-$6^B,6^C,6^D,6^E,6^F,6^G$-hexa-O-methyl-$\beta$-cyclodextrin $\beta$-Cyclodextrin (Aldrich) was dried with $P_2O_5$ under vacuum at 100° for 24 h before use. Mono(6-O-toluenesulfonyl)-$\beta$-cyclodextrin was conveniently prepared from $\beta$-cyclodextrin in a 31% yield following the procedure as reported by Matsui, et al. *Bull. Chem. Soc. Jpn.* 1978, 51, 3030. Nucleuphilic azido substitution and permethylation of mono(6-O-toluenesulfonyl)-$\beta$-cyclodextrin 1 were accomplished in situ to produce permethylated 6-azido-6-deoxy-$\beta$-cyclodextrin as follows.

A mixture of 1 (16.53 g, 12.8 mmol) and $NaN_3$ (5.00 g, 76.9 mmol) in 300 mL of DMF was stirred at 120° C. for 100 min. After being cooled to room temperature and filtered, the solution was added dropwise to a suspension of NaH (18.46 g, 0,769 mol) in 700 mL of DMF and then iodomethane (120.07 g, 0.846 mol) was dropped slowly into the above mixture at 0° C. Stirring was continued at room temperature for 24 h. Into the reaction mixture was slowly added 20 mL of $CH_3OH$ at 0°

C. to decompose the excess NaH, and stirring was continued for 1 h. Most of DMF was distilled under reduced pressure and the residue was partitioned between CHCl$_3$ and water. The organic layer was separated, washed successively with water, aqueous Na$_2$S$_2$O$_3$ and water and then dried and concentrated. The residual DMF was removed in vacuum. The crude product was chromatographed on silica gel (CHCl$_3$: CH$_3$OH/80:1) to afford pure 6$^A$-azido-6$^A$-deoxyheptakis(2,3-di-O-methyl)-6$^B$,6$^C$,6$^D$,6$^E$,6$^F$,6$^G$-hexa-O-methyl-$\beta$-cyclodextrin; mp 97°–99° C.; [$\alpha$]$_{25}$D+155.1° (c 1.37, CHCl$_3$); IR (KBr) $\nu$ 2924, 2100, 1458, 1400, 1158, 1107, 1041, 971 cm$^{-1}$; $_1$H NMR $\delta$ 5.16–5.00 (m, 7H), 4.00–3.26 (m, 95H), 3.17 (dd, J$_1$=3.0 Hz, J$_2$=9.24 Hz, 7H); $^{13}$C NMR $\delta$ 99.6, 99.5, 99.4, 82.6, 82.4, 82.3, 81.9, 80.8, 80.7, 80.6, 71.9, 71.6, 71.4, 71.3, 672.0, 61.8, 59.4, 59.0, 58.9, 52.8. Anal. Calcd for C$_{62}$H$_{109}$N$_3$O$_{34}$: C, 51.69; H, 7.63; N, 2.92. Found: C, 51.49; H, 7.49; N, 2.88.

EXAMPLE 18

6$^A$-Amino-6$_A$-deoxyheptakis(2,3-di-O-methyl)-6$^B$,6$^C$,6$^D$,6$^E$,6$^F$,6$^G$-hexa-O-methyl-$\beta$-cyclodextrin The azido cyclodextrin produced in Example 17 was directly hydrogenated in the presence of PtO$_2$ catalyst in ethanol to yield the corresponding amino derivative as follows.

A solution of the azido cyclodextrin of Example 17 (16.06 g, 11.2 mmol) in 200 mL of C$_2$H$_5$OH was shaken with PtO$_2$ (0.65 g) at room temperature for 4 days with hydrogen (50 psi). The mixture was filtered through a Celite 545 pile and the filtrate was evaporated to dryness under reduced pressure. The residue was purified by column chromatography (CHCl$_3$:CH$_3$OH/20:0) to give 11.67 g (74% yield) of 6$^A$-amino-6$_A$-deoxyheptakis(2,3-di-O-methyl)-6$^B$,6$^C$,6$^D$,6$^E$,6$^F$,6$^G$-O-methyl-$\beta$-cyclodextrin; mp 91°–93° C.; [$\alpha$]$^{25}$D+143.4° (c 0.93, CHCl$_3$); IR(KBr) Y3434, 29271 1508, 1458, 1400, 143, 1108, 1040, 971 cm$^{-1}$; $^1$H NMR $\delta$ 5,20–4.96 (m, 7H), 3.94–3.24 (m, 95H), 3.16 (dd, J$_1$=3.30 Hz, J$_2$=9.44 Hz, 7H), 3.00 (s, NH, 2H); $^{13}$C NMR $\delta$ 99.5, 99.4, 99.3, 83.1, 82.5, 82.4, 82.2, 81.0, 80.9, 80.6, 80.4, 77.7, 72.1, 71.7, 71.6, 71.4, 71.3, 69.6, 62.0, 61.8, 61.6, 59.6, 59.4, 59.1, 58.9, 58.7, 43.2. Anal. Calcd. for C$_{62}$H$_{111}$NO$_{34}$H$_2$O: C, 51.34; H, 7.99; N, 0.97. Found: C, 51.44; H, 7,80; N, 0.99.

EXAMPLE 19

6$^A$-[p-Allyloxy)benzamido]-6$^A$-deoxyheptakis(2,3-di-O-methyl)-6$^B$,6$^C$,6$^D$,6$^E$,6$^F$,6$^G$-hexa-O-methyl-$\beta$-cyclodextrin (4)

Treatment of amino cyclodextrin of Example 18 with an excess of p-allyloxy)benzoyl chloride in the presence of NE$_{t3}$ in toluene gave permethylated mono-(p-allyloxy)benzmido-$\beta$-cyclodextrin in a yield of 86%. The procedure was carried out as follows.

A solution of p-(allyloxy)benzoyl chloride (1.70 g, 8.66 mmol) in 100 mL of toluene was added dropwise to a stirring solution of the amino cyclodextrin (11.67 g, 8.25 mmol) and NE$_{t3}$ (2.00 g, 19.8 mmol) in 150 mL of toluene at room temperature over 1 h. The mixture was stirred at room temperature for 24 h. The mixture was filtered and the filtrate was diluted with 150 mL of toluene and washed twice with water. The organic layer was dried and concentrated. The residue was crystallized from ethyl ether hexane to give white crystals of 6$^A$-[p-allyloxy)benzamido]-6$^A$-deoxyheptakis(2,3-di-O-methyl)-6$^B$,6$^C$,6$^D$, 6$^E$,6$^F$,6$^G$-hexa-O-methyl-$\beta$-cyclodextrin (11.08 g, 86% yield); mp 110°–112° C.; [$\alpha$]$_D^{25}$+141.0° (c 1.40, CHCl$_3$); IR(KBr) $\nu$ 3446, 2930,2832, 1654, 1606, 1499, 1458, 1384, 1249, 1161,1109, 1038, 973, 853, 755, 706; $^1$H NMR $\delta$ 7.73 (d,J=8.73 Hz, 2H), 6.90 (d, J=8.73 Hz, 2H), 6.72 (broad s, 1H), 6.03 (m, 1H), 5.46–4.99 (m, 9H), 4.53 (d,J=3.22 Hz, 2H), 4.20–3.05 (m, 102 Hz); C NMR $\delta$ 167.3, 161.6, 133.1, 129.3, 127.4, 118.5, 100.1, 99.5, 99.4, 99.3, 82.9, 82.6, 82.5, 82.3, 82.2, 82.0, 81.2, 81.1, 81.0, 80.5, 80.3, 77.8, 72.1, 71.9, 71.6, 71.5, 71.3, 70.8, 69.3, 62.1, 62.0, 61.8, 61.7, 61.6, 59.8, 59.4, 59.2, 58.9, 58.8, 58.6, 41.0; Anal. Calcd for C$_{72}$h$_{119}$NO$_{36}$: C, 54.40; H, 7.70; N. 0.90. Found: C, 54.20; H, 7.55; N, 0.84.

Synthesis of 2 and 3-Position Functionalized Cyclodextrin Monomers

As in the case of the 6-substituted cyclodextrins reported above, proton and carbon NMR spectra were of the 2 and 3-position functionalized cyclodextrins were recorded in CDCl$_3$ at 200 MHz. $\beta$-Cyclodextrin (Aldrich) was dried with P$_2$O$_5$ under vacuum at 100° C. for 24 h before use. Organic extracts were dried over anhydrous MgSO$_4$. Heptakis[6-O-(tert-butyl)dimethylsilyl]-$\beta$-cyclodextrin was prepared as reported.[1] Yi, et al, J. Org. Chem. 1993, 58, 2561.

3-Position Functionalized Cyclodextrin Monomers

EXAMPLE 20

Heptakis(2,6-di-O-methyl)-$\beta$-cyclodextrin.

Heptakis(2,6-di-O-methyl)-$\beta$-cyclodextrin was prepared from native $\beta$-cyclodextrin in a 55% yield as reported by Casu, et al., Tetrahedron 1968, 24, 803 and Szejtli, et al., Starch/Starke 1980, 32, 165.

A mixture of 46.7 g (0.24 mol) of BaO and 46.7 g (0.14 tool) of Ba(OH)$_2$8H$_2$O was slowly added at room temperature to a stirred solution of $\beta$-cyclodextrin (22.7 g, 0.02 mol) and dimethyl sulfate (93.3 g, 0.98 mol) in 280 mL of a 1:1 mixture of DMSO and DMF. The mixture was stirred at room temperature for 7 days, and the solvent was removed by vacuum distillation. The residue was extracted five times by 200 mL portions of hot CHCl$_3$ and the extract solution was washed with water, dried and concentrated. The crude product was dried under vacuum at 60° C. for 24 h to remove traces of DMSO and DMF, and then subjected to column chromatography on silica gel (CH$_3$C$_6$H$_5$:C$_2$H$_5$OH/20:1) to give crystalline heptakis (2,6-di-O-methyl)-$\beta$-cyclodextrin (14.7 g, 55% yield); mp 312°–314° C. (lit.$^5$ 312° C.); [$\alpha$]$_D^{25}$+123.9° (C, 0.84, CHCl$_3$) (lit.$^5$ 122° ); $^1$H NMR $\delta$ 5.05 (s, 7H, OH), 4.95 (d, J=3.28 Hz, 7H), 3.90 (overlapping dd, J$_1$=9.79 Hz, J$_2$=9.39 Hz, 7H), 3.81–3.30 (m, 70H), 3.24 (dd, J$_1$=3.28 Hz, J$_2$=9.79 Hz, 7H); $^{13}$C NMR $\delta$ 101.8, 84.1, 82.6, 73.7, 71.4, 70.8, 60.8, 59.4. Anal. Calcd. for C$_{56}$H$_{98}$O$_{35}$: C, 50.52; H, 7.42. Found: C, 50.69: H, 7.23 .

EXAMPLE 21

3-O-(p-Allyloxybenzoyl)heptakis(2,6-di-O-methyl)-$\beta$-cyclodextrin

The cyclodextrin of Example 20 was treated with p-allyloxybenzoyl chloride in dry pyridine at 100° C. to produce 3-O-(p-allyloxybenzoyl)heptakis(2,6-di-O-methyl)-$\beta$-cyclodextrin which was purified by silica gel chromatography as follows.

A solution of of the cyclodextrin of Example 20 (2.66 g, 2.0 mmol) and p-allyloxybenzoyl chloride (1.20 g, 6.0 mmol) in 100 mL of dry pyridine was stirred at 100° C. for 2 days. Pyridine was removed by vacuum distillation. A solution of the residue in CHCl$_3$ was washed with water, dried and concentrated. Column chromatography (CHCl$_3$:CH$_3$OH/100:1) of crude product gave 0.45 g (15% yield) of 3-O-(p-allyloxybenzoyl)heptakis(2,6-di-O-methyl)-β-cyclodextrin; mp 273°–275° C.; $[\alpha]_D^{25}$ +120.0° (c, 0.35, CHCl$_3$); $^1$H NMR δ 8.01 (d, J=8.82 Hz, 2H), 6.89 (d, J=8.82 Hz, 2H), 6.00 (m, 1H), 5.45–5.22 (m, 4H), 5.08 (s, 6 H, OH), 5.00–4.86 (m, 4H), 4.82 (d, J=3.33 Hz, 1H), 4.71 (d, J=3.33 Hz, 1H), 4.53 (d, J=5.22 Hz, 2H), 4.05–2.98 (m, 83H); $^{13}$C NMR δ 165.5,133.1, 133.0, 132.2, 124.1, 118.5, 118.4, 114.6, 102.2, 102.0, 101.8, 101.7, 101.6, 84.9, 84.8, 84.7, 84.5, 84.4, 84.3, 84.1, 84.0, 83.8, 82.8, 82.5, 82.3, 81.8, 81.6, 81.5, 79.9, 78.4, 73.6, 73.5, 72.8, 72.6, 72.3, 72.2, 72.1, 71.8, 71.6, 71.4, 70.9, 70.6, 70.4, 69.3, 69.1, 61.2, 60.9, 60.8, 60.7, 59.6, 59.5, 59.4, 59.3. Anal. Calcd for C$_{66}$H$_{106}$O$_{37}$: C, 53.15; H, 7.16. Found: C, 53.30; H, 7.35.

EXAMPLE 22

3$^A$-O-(p-Allyloxybenzoyl)heptakis(2,6-di-O-methyl)-3$^B$,3$^C$,3$^D$,3$^E$,3$^F$,3$^G$-hexa-O-methyl-β-cyclodextrin Methylation of the cyclodextrin of Example 21 with methyl triflate and 2,6-di(tert-butyl)-4-methylpyridine in CH$_2$Cl$_2$ provided the allyloxybenzoyl derivative of this example in an excellent yield. Synthesis proceeded as follows.

A solution of the product of Example 21 (0.23 g, 0.15 mmol), 2,6-di-(tert-butyl)-4-methylpyridine (0.38 g, 1.9 mmol) and methyl triflate (0.23 g, 1.4 mmol) in 5 mL of CH$_2$Cl$_2$ was stirred in a capped Teflon tube at 80° C. for 2.5 h. After being dried and concentrated the crude product was purified by column chromatography (CHCl$_3$:CH$_3$OH/100:1) to yield pure 3$^A$-O-(p-allyloxybenzoyl)heptakis(2,6-di-O-methyl)-3$^B$,3$^C$,3$^D$,3$^E$,3$^F$,3$^G$-hexa-O-methyl-β-cyclodextrin (0.19 g, 79% yield); mp 243°–244° C.; $[\alpha]_D^{25}$ +105.1° (c, 1.16, CHCl$_3$); $^1$H NMR δ 8.04 (d, J=8.83 Hz, 2H), 6.91 (d, J=8.83 Hz, 2H), 6.04 (m, 1H), 5.48–5.20 (m, 4H), 5.17–5.05 (m, 4H), 5.03 (d, J=3.30 Hz, 1H), 4.90 (d, J=3.30 Hz, 1H), 4.59 (d, J=5.24 Hz, 2H), 4.07 –3.28 (m, 95H), 3.18 (dd, J$_1$=3.30, J$_2$=9.60, 6H); $^{13}$C NMR δ 164.8, 133.1, 132.2, 124.1, 118.5, 114.4, 100.0, 99.8, 99.6, 99.3, 83.0, 82.9, 82.6, 82.5, 82.3, 82.2, 82.1, 82.0, 81.5, 81.3, 81.0, 80.8, 80.7, 79.2, 72.6, 72.0, 71.9, 71.7, 71.6, 71.4, 71.3, 71.2, 71.1, 71.0, 69.6, 69.3, 62.2, 62.0, 61.9, 61.8, 61.6, 60.0, 59.5, 59.4, 59.3, 59.1, 58.9, 58.7, 58.6. Anal. Calcd for C$_{72}$H$_{118}$O$_{37}$: C, 54.88; H, 7.55. Found: C, 54.85; H, 7.92.

2-Position Functionalized Cyclodextrin Monomers

Some selective mono-functionalization of the hydroxy groups at the 2-positions of native β-cyclodextrin has been done by other groups. Ueno, et al., *Tetrahedron Lett.* 1982, 23, 3451; Rong, et al., *Tetrahedron Lett.* 1990, 31, 4275 and Rao, et al., *J. Org. Chem.* 1991, 56, 1327. In the present situation the use of heptakis[6-O-(tert-butyl)dimethylsilyl]-δ-cyclodextrin was preferred as a starting material to make mono-2-O-alkenyl-β-cyclodextrin derivatives.

EXAMPLE 23

2-O-(p-Allyloxybenzoyl)heptakis[6-O-(tert-butyl)dimethylsilyl]-β-cyclodextrin

Treatment of heptakis[6-O-(tert-butyl)dimethylsilyl]-β-cyclodextrin with p-allyloxybenzoyl chloride and triethylamine in toluene gave 2-O-(p-allyloxybenzoyl)-heptakis[6-O-(tert-butyl)dimethylsilyl]-β-cyclodextrin as follows.

A mixture of heptakis[6-O-(tert-butyl)dimethylsilyl]-β-cyclodextrin (5.0 g, 2.6 mmol), p-allyloxybenzoyl chloride (0.5 g, 2.6 mmol) and NEt$_3$ (0.31 g, 3.1 mmol) in 50 mL of toluene was stirred at room temperature for 24 h. The mixture was diluted with 50 mL of toluene and washed successively with cold 3% HCl, 5% aqueous NaHCO$_3$, and water. The organic layer was dried and concentrated. The residue was chromatographed on silica gel (CHCl$_3$: CH$_3$OH/20:1) to produce pure 2-O-(p-allyloxybenzoyl)heptakis[6-O-(tert-butyl) dimethylsilyl]-β-cyclodextrin (1.12 g, 21% yield); mp 255°–256° C.; $[\alpha]_D^{25}$+105.8° (c, 3.91, CHCl$_3$); $^1$H NMR δ 7.95 (d, J=8.85 Hz, 2H), 6.87 (d, J=8.85 Hz, 2H), 6.02 (m, 1H), 5.70–5.15 (m, 15H), 5.11 (d, J=3.28 Hz, 1H), 5.01–4.73 (m, 7H), 4.54 (d, J=5.22 Hz, 2H), 4.26 –3.25 (m, 41H), 0.90 (s, 63H), 0.05 (s, 42H); $^{13}$C NMR δ 166.8, 133.1, 133.0, 132.7, 132.4, 122.2, 118.5, 115.0, 103.2, 102.7, 102.6, 102.5, 102.1, 100.7, 82.5, 82.2, 74.7, 74.6, 74.3, 74.0, 73.8, 73.5, 73.3, 73.2, 73.0, 72.7, 69.3, 69.2, 62.1, 26.4, 26.3, 19.0, 18.8, 18.7, −4.6, −4.7, −4.8. Anal. Calcd for C$_{94}$H$_{176}$O$_{37}$Si$_7$: C, 53.89; H, 8.47. Found: C, 53.87; H, 8.22.

EXAMPLE 24

2-O-[p-(tert-Butyl)benzoyl]heptakis[6-O-(tert-butyl)-dimethylsilyl]-βcyclodextrin Treatment of heptakis [6-O-(tert-butyl) dimethylsilyl]-β-cyclodextrin with p-(tert-butyl)benzoyl chloride and triethylamine in toluene gave 2-O-[p-(tert-butyl)benzoyl]heptakis[6-O-(tert-butyl)dimethylsilyl]-β-cyclodextrin as follows.

This cyclodextrin derivative was prepared as in Example 23 from 9.7 g (5.0 mmol) of heptakis [6-O-(tert-butyl) dimethylsilyl]-β-cyclodextrin, 1.0 g (5.0 mmol) of p-(tert-butyl)benzoyl chloride and 0.56 g (5.5 mmol) of NEt$_s$ to give 2.00 g (19% yield) of 2-O-[p-(tert-butyl)-benzoyl]heptakis[6-O-(tert-butyl)dimethylsilyl]-β-cyclodextrin; mp 264°–266° C.; $[\alpha]_D^{25}$+102.6° (c, 3.50, CHCl$_3$); $^1$H NMR δ 7.97 (d, J=8.54 Hz, 2H), 7.43 (d, J=8.54 Hz, 2H), 5.50 (broad s, 13 H, OH), 5.39 (d, J=3.23 Hz, 1H), 5.00–4.75 (m, 7H), 4.46–3.30 (m, 41H), 1.29 (s, 9H), 0.88 (s, 63H), 0.05 (s, 42H); $^{13}$C NMR δ 166.2, 130.3, 127.8, 125.8, 102.6, 102.5, 102.4, 82.2, 77.6, 74.3, 74.1, 73.9, 73.6, 73.5, 73.3, 73.2, 73.0, 72.8, 72.7, 72.4, 62.2, 62.1, 35.5, 31.6, 26.7, 26.5, 26.4, 26.3, 26.1, 19.0, 18.8, 18.7. Anal. Calcd for C$_{95}$H$_{180}$O$_{36}$Si$_7$: C, 54.46; H, 8.66. Found: C, 54.62; H, 8.49.

EXAMPLE 25

2$^A$-O-(p-Allyloxybenzoyl)heptakis[3-O-acetyl-6-O-(tert-butyl)dimethylsilyl]-2$^B$,2$^C$,2$^D$,2$^E$,2$^F$,2$^G$-hexa-O-acetyl-β-cyclodextrin Acylation of the cyclodextrin of Example 23 with acetic anhydride in pyridine gave the tridecaacetate in a 73% yield as follows.

A solution of 2-O-(p-allyloxybenzoyl)heptakis[6-O-(tert-butyl)dimethylsilyl]-β-cyclodextrin (0.84 g, 0.40 mmol) in 30 mL of acetic anhydride and 30 mL of pyridine was stirred at 100° C. for 4 h. The solvent was removed under reduced pressure and the residue was dissolved in CHCl$_3$. The solution was washed with water twice, dried and concentrated. The crude product was purified by column chromatography (CH$_3$C$_6$H$_5$:C$_2$H$_5$OH/200:3) to give 2$^A$-O-(p-allyloxybenzoyl)heptakis[3-O-acetyl-6-O-(tert-butyl)dimethylsilyl]-2$^B$,2$^C$,2$^D$,2$^E$,2$^F$,2$^G$-hexa-O-acetyl-β-cyclodextrin (0.77 g, 73% yield); mp 136°–138° $[\alpha]_D^{25}$+89.8° (c, 0.93, CHCl$_3$); $^1$H NMR δ 7.97 (d, J=8.83 Hz, 2H), 6.97 (d, J=8.83 Hz, 2H), 6.06 (m, 1H), 5.50–5.22 (m, 10H), 5.22–5.08 (m, 6H), 4.90 (dd, J$_1$=9.61 Hz, J$_2$=3.28 Hz, 1H), 4.70 (dd, J$_1$=9.61 Hz, J$_2$=3.28 Hz, 6H), 4.59 (d, J=5.22 Hz, 2H), 4.17–3.64 (m, 28H), 2.17–1.75 (m, 39H), 0.90 (s, 63H), 0.06 (s, 42H); $^{13}$C NMR δ

171.3, 171.2, 171.1, 171.0, 170.0, 169.8, 169.5, 166.5, 133.1, 132.8, 122.1, 118.5, 114.9, 100.0, 96.8, 96.6, 77.7, 75.8, 75.7, 75.6, 72.6, 72.3, 72.2, 72.1, 71.9, 71.8, 71.7, 69.6, 69.3, 62.4, 62.3, 62.2, 26.3, 21.4, 21.2, 18.3, −4.5, −4.7, −4.8. Anal. Calcd for $C_{120}H_{202}O_{50}Si_7$: C, 54.56; H, 7.71. Found: C, 54.36; H, 7.70.

EXAMPLE 26

$2^A$-O-(p-Allyloxybenzoyl)heptakis(3-O-acetyl)-$2^B,2^C,2^D,2^E,2^F,2^G$-hexa-O-acetyl-β-cyclodextrin The silyl groups of the compound of Example 25 were removed with $BF_3$-$OEt_2$ in $CH_2Cl_2$ to produce $2^A$-O-(p-allyloxybenzoyl) heptakis(3-O-acetyl)-$2^B,2^C,2^D,2^E,2^F,2^G$-hexa-O-acetyl-β-cyclodextrin in a yield of 78% as follows.

A solution of $2^A$-O-(p-allyloxybenzoyl)heptakis[3-O-acetyl-6-O-(tert-butyl)dimethylsilyl]-$2^B,2^C,2^D,2^E,2^F,2^G$-hexa-O-acetyl-β-cyclodextrin (0.70 g, 0.27 mmol) in 15 mL of $CH_2Cl_2$ was stirred with $BF_3$-$OEt_2$ (0.32 g, 2.2 mmol) at room temperature for 6 h. The mixture was diluted with $CH_2Cl_2$ and poured into ice-water. The organic layer was separated, washed with water, aqueous $NaHCO_3$ and water, and then dried and concentrated. Column chromatography ($CHCl_3$:$CH_3OH$/7:1, then 4: 1) of the residue gave $2^A$-O-(p-allyloxybenzoyl)-heptakis (3-O-acetyl)-$2^B,2^C,2^D,2^E,2^F,2^G$-hexa-O-acetyl-β-cyclodextrin (0.38 g, 78%); mp 178°-179° C.; $[α]_D^{25}=102.8°$ (c, 1.07, $CHCl_3$); $^1H$ NMR δ 7.95 (d, J=8.72 Hz, 2H), 6.95 (d, J=8.72 Hz, 2H), 6.03 (m, 1H), 5.89-5.50 (m, 10H), 5.50-5.17 (m, 6H), 5.17-4.62 (m, 14H), 4.57 (d, J=5.24 Hz, 2H), 4.40-3.40 (m, 28H), 2.30-1.80 (m, 39H); $^{13}C$ NMR δ 171.3, 171.2, 171.1, 169.8, 169.7, 166.5, 133.1, 133.0, 122.1, 118.6, 114.9, 97.4, 97.3, 97.2, 77.7, 73.0, 72.9, 72.8, 72.7, 72.5, 72.4, 72.3, 72.2, 72.1, 72.0, 71.9, 71.8, 71.7, 71.6, 71.5, 71.4, 71.3, 71.2, 71.1, 71.0, 70.8, 69.3, 61.2, 21.3, 21.2. Anal. Calcd for $C_{78}H_{104}O_{50}$: C, 50.87; H, 5.69. Found: C, 50.96; H, 5.71.

EXAMPLE 27

$2^A$-O-(p-Allyloxybenzoyl)heptakis(3-O-acetyl-6-O-methyl)-$2^B,2^C,2^D,2^E,2^F,2^G$-hexa-O-acetyl-β-cyclodextrin Methylation of the compound of Example 26 with methyl triflate and 2,6-di (tert-butyl)methylpyridine in $CH_2Cl_2$ gave $2^A$-O-(p-allyloxybenzoyl)heptakis(3-O-acetyl-6-O-methyl)-$2^B,2^C,2^D,2^E,2^F,2^G$-hexa-O-acetyl-β-cyclodextrin as follows.

A mixture of the Example 26 cyclodextrin (0.38 g, 0.21 mmol), methyl triflate ( 0.49 mL, 4.3 mmol) and 2,6-di(tert-butyl)-4-methylpyridine (1.2 g, 5.8 mmol) in 6 mL of $CH_2Cl_2$ was heated in a sealed tube at 80° C. for 2.5 h and cooled. $CH_3OH$ (6 mL) was added, and the mixture was stirred at room temperature for 1 h, and concentrated. A solution of the residue in $CHCl_3$ was washed successively with water, cold 3% HCl, aqueous $NaHCO_3$, and water, and then dried and concentrated. The product was subjected to column chromatography ($CHCl_3$: $CH_3OH$/20:1) to give $2^A$-O-(p-allyloxybenzoyl)heptakis(3-O-acetyl-6-O-methyl)-$2^B,2^C,2^D,2^E,2^F,2^G$-hexa-O-acetyl-β-cyclodextrin (0.19 g, 50% yield); mp 127°-128° C.; $[α]_D^{25}$100.2° (c, 1.85, $CHCl_3$); $^1H$ NMR δ 7.95 (d, J=8.78 Hz, 2H), 6.94 (d, J=8.78 Hz, 2H), 6.02 (m, 1H), 5.62-5.19 (m, 10H), 5.19-5.00 (m, 6H), 4.95 (dd, $J_1$=9.67 Hz, $J_2$=3.32 Hz, 1H), 4.78 (dd, $J_1$=9.67 Hz, $J_2$=3.32 Hz, 6H), 4.57 (d, J=5.22 Hz, 2H), 4.10-3.70 (m, 21H), 3.65-3.43 (m, 7H), 3.38 (s, 21H), 2.15-1.70 (m, 39H); $^{13}C$ NMR δ 171.2, 171.1, 170.1, 169.8, 169.5, 166.4, 133.0, 132.8, 121.2, 118.5, 114.9, 97.6, 96.9, 76.5, 76.2 75.7, 71.7, 71.3, 71.1, 70.9, 69.3, 59.6, 21.3, 21.1. Anal. Calcd for $C_{85}H_{118}O_{50}$: C, 52.63; H, 6.13. Found: C, 52.45; H, 6.34.

EXAMPLE 28

$2^A$-O-(p-Allyloxybenzoyl)heptakis[6-O-(tert-butyl)-dimethylsilyl-3-O-methyl]-$2^B,2^C,2^D,2^E,2^F,2^G$-hexa-O-methyl-β-cyclodextrin The cyclodextrin of Example 23 was methylated under mild conditions to produce permethylated $2^A$-O-benzoyl-substituted heptakis[6-O-(tert-butyl)dimethylsilyl]-β-cyclodextrin as followed.

A mixture of the cyclodextrin of Example 23 (0.80 g, 0.38 mmol), 2,6-di(tert-butyl)-4-methylpyridine (2.6 g, 12.5 mmol) and methyl triflate (1.6 g, 10 mmol) in 6 mL of $CH_2Cl_2$ was stirred in a capped Teflon tube at 80° C. for 2.5 h. After being cooled, 10 mL of $CH_3OH$ was added, and the mixture was stirred at room temperature for 1 h. The solvent was removed under a reduced pressure to yield a solid mixture, which was dissolved in $CH_2Cl_2$. The organic solution was washed successively with 3% cold HCl, 5% aqueous $NaHCO_3$ and water, and then dried and concentrated. Crude product was chromatographed ($C_6H_{14}$:$CH_3CO_2C_2H_5OH$/80:20:1) to give 0.65 g (75% yield) of $2^A$-O-(p-Allyloxybenzoyl)-heptakis[6-O-(tert-butyl)dimethylsilyl-3-O-methyl]-$2^B,2^C,2^D,2^E,2^F,2^G$-hexa-O-methyl-β-cyclodextrin; mp 136°-138° C.; $[α]_D^{25}=97.5°$ (c, 2.68, $CHCl_3$); $^1H$ NMR δ 8.08 (d, J=8.67 Hz, 2H), 6.87 (d, J=8.67 Hz, 2H), 6.04 (m, 1H), 5.49-5.10 (m, 9H), 4.92 (dd, $J_1$=3.28 Hz, $J_2$=9.72 Hz, 1H), 4.57 (d, J=5.26 Hz, 2H), 4.23-3.30 (m, 74H), 3.05 (dd, $J_1$=3.28 Hz, $J_2$=9.72 Hz, 6H), 0.88 (s, 63H), 0.05 (s, 42H); $^{13}C$ NMR δ 166.1, 133.1, 132.4, 123.4, 118.5, 114.6, 98.7, 98.6, 98.5, 98.2, 97.6, 82.9, 82.7, 82.6, 82.4, 82.3, 80.8, 79.4, 79.3, 79.2, 78.9, 78.7, 77.0, 72.3, 72.7, 72.6, 69.3, 62.7, 62.1, 62.9, 61.8, 61.3, 59.2, 59.0, 58.9, 58.8, 26.4, 18.8, −4.4, −4.5, −4.7, −4.8. Anal. Calcd for $C_{107}H_{202}O_{37}Si_7$: C, 56.43; H, 8.94. Found: C, 56.53; H, 9.01.

EXAMPLE 29

$2^A$-O-[p-(tert-Butyl)benzoyl]heptakis[6-O-(tert -butyl)-dimethylsilyl-3-O-methyl]-$2^B,2^C,2^D,2^E,2^F,2^G$-hexa-O-methyl-β-cyclodextrin The cyclodextrin of Example 23 was methylated under mild conditions as in Example 28 to produce permethylated $2^A$-O-benzoyl-substituted heptakis[6-O-(tert-butyl)dimethylsilyl]-β-cyclodextrin.

Following the procedure of Example 28 2.0 g (1.0 mmol) of 2-O-p-(tert-butyl)benzoyl]heptakis [6-O-(tert-butyl) dimethylsilyl]-β-cyclodextrin, 3.8 g (18.3 mmol) of 2,6-di (tert-butyl)-4-methylpyridine and 2.43 g (14.8 mmol) of methyl triflate to produce 1.72 g (80% yield) of $2^A$-O-benzoyl-substituted heptakis[6-O-(tert-butyl)-dimethylsilyl]-β-cyclodextrin; mp 148°-150° C.; $[α]_D^{25}$+93.0° (c, 2.11, $CHCl_3$); $^1H$ NMR δ 8.06 (d, J=8.83 Hz, 2H), 7.40 (d, J=8.83 Hz, 2H), 5.47 (d, J=3.32 Hz, 1H), 5.30-5.10 (m, 6H), 4.97 (dd, $J_1$=3.32 Hz, $J_2$=9.65 Hz, 1H), 4.29-3.30 (m, 74H), 3.15-2.92 (m, 6H), 1.34 (s, 9H), 0.89 (s, 63H), 0.07 (s, 42H); $^{13}C$ NMR δ 166.2, 130.2, 128.0, 125.6, 98.7, 98.6, 98.4, 98.0, 82.6, 82.5, 82.3, 80.8, 79.5, 79.4, 79.2, 76.9, 74.2, 72.7, 72.6, 72.5, 62.7, 62.2, 62.0, 61.8, 61.3, 59.4, 59.1, 58.9, 58.6, 35.6, 31.6, 26.4, 18.8, −4.4, −4.5, −4.6, −4.8. Anal. Calcd for $C_{108}H_{206}O_{36}Si_7$: C, 56.96; H, 9.12. Found: C, 57.16; H, 8.95.

EXAMPLE 30

$2^A$-O-(p-Allyloxybenzoyl)heptakis(3-O-methyl)-$2^B,2^C,2^D,2^E,2^F,2^G$-hexa-O-methyl-β-cyclodextrin The cyclodextrin of Example 28 was transformed into a heptaol by treatment with NH$_4$F in CH$_3$OH as follows.

A solution of $2^A$-O-(p-Allyloxybenzoyl)heptakis[6-O-(tert-butyl)dimethylsilyl-3-O-methyl]-$2^B,2^C,2^D,2^E,2^F,2^G$-hexa-O-methyl-β-cyclodextrin (0.62 g, 0.27 mmol) in 100 mL of CH$_3$OH was refluxed with NH$_4$F (0.71 g, 19.1 mmol) for 24 h and evaporated to dryness. A solution of the residue in CHCl$_3$ was washed with water twice, dried and concentrated. Crude product was subjected to column chromatography (CHCl$_3$:CH$_3$OH/8:1) to yield 0.34 g (85% yield) of $2^A$-O-(p-Allyloxybenzoyl)heptakis(3-O-methyl)-$2^B,2^C,2^D,2^E,2^F,2^G$-hexa-O-methyl-β-cyclodextrin; mp 175°–176° C.; $[\alpha]_D^{25}$ +156 2° (C 1.15, CHCl$_3$); $^1$H NMR δ 8.05 (d, J=8.63 Hz, 2H), 6.91 (d, J=8.63 Hz, 2H), 6.04 (m, 1H), 5.50–5.25 (m, 3H), 5.20–5.00 (m, 6H), 4.89 (dd, J$_1$=3.29 Hz, J$_2$=9.56 Hz, 1H), 4.72 (s, 7H, OH), 4.57 (d, J=5.29 Hz, 2H), 4.12–2.95 (m, 80H); $^{13}$C NMR δ 166.3, 133.0, 132.4, 123.1, 118.6, 114.8, 99.1, 99.0, 82.5, 82.4, 82.1, 80.8, 77.7, 74.5, 73.0, 72.9, 72.8, 69.6, 69.3, 62.0, 61.8, 61.7, 61.4, 59.2, 59.0, 58.9. Anal. Calcd for C$_{65}$H$_{104}$O$_{37}$: C, 52.84; H, 7.09. Found: C, 52.87; H, 7.00.

EXAMPLE 31

$2^A$-O-[p-(tert-Butyl)benzoyl]heptakis(3-O-methyl)-$2^B,2^C,2^D,2^E,2^F,2^G$-hexa-O-methyl-β-cyclodextrin The procedure of Example 30 was followed using the cyclodextrin of Example 28.

A solution containing 0.88 g (0.39 mmol) of $2^A$-O-benzoyl-substituted heptakis[6-O-(tert-butyl)dimethylsilyl]-β-cyclodextrin and 0.61 g (16.2 mmol) of NH$_4$F were treated as in Example 30 to give 0.53 g (93% yield) of $2^A$-O-[p-(tert-butyl)benzoyl]heptakis(3-O-methyl)-$2^B,2^C,2^D,2^E,2^F,2^G$-hexa-O-methyl-β-cyclodextrin; mp 197°–199° C.; $[\alpha]_D^{25}$ +150.3 25 (c, 1.54, CHCl$_3$); $^1$H NMR δ 8.02 (d, J=8.57 Hz, 2H), 7.42 (d, J=8.57 Hz, 2H), 5.30 (d, J=3.31 Hz, 1H), 5.25–4.98 (m, 6H), 4.89 (dd, J$_1$=3.31 Hz, J$_2$=9.65 Hz, 1H), 4.73 (broad s, 7H, OH), 4.12–3.29 (m, 74H), 3.29–3.03 (m, 6H), 1.33 (s, 9H); $^{13}$C NMR δ 166.6, 130.3, 127.7, 125.8, 99.4, 99.2, 99.1, 82.5, 82.4, 82.2, 82.0, 81.9, 81.0, 80.8, 79.8, 77.7, 73.1, 73.0, 72.9, 72.8, 72.7, 62.1, 61.9, 61.7, 61.5, 58.8, 35.6, 31.6. Anal. Calcd for C$_{66}$H$_{108}$O$_{36}$: C, 53.64; H, 7.37. Found: C, 53.63; H, 7.42.

EXAMPLE 32

$2^A$-O-(p-Allyloxybenzoyl)heptakis(3,6-di-O-methyl)-$2^B,2^C,2^D,2^E,2^F,2^G$-hexa-O-methyl-βcyclodextrin A permethylated monoalkenyl-β-cyclodextrin was prepared as in Example 27 from 0.19 g (0.13 mmol) of $2^A$-O-(p-Allyloxybenzoyl)heptakis(3-O-methyl)-$2^B,2^C,2^D,2^E,2^F,2^G$-hexa-O-methyl-β -cyclodextrin, 0.37 g (1.80 mmol) of 2,6-di(tert-butyl)-4-methylpyridine and 0.22 g (1.35 mmol) of methyl triflate to give $2^A$-O-(p-allyloxybenzoyl)heptakis(3,6-di-O-methyl)-$2^B,2^C,2^D,2^E,2^F,2^G$-hexa-O-methyl-β-cyclodextrin (0.10 g, 59% yield); mp 107°–109° C.; $[\alpha]_D^{25}$ +130°-7° (c, 0.99, CHCl$_3$); $^1$H NMR δ 8.10 (d, J=8.90 Hz, 2H), 6.90 (d, J=8.90 Hz, 2H), 6.04 (m, 1H), 5.48–5.21 (m, 3H), 5.18–5.05 (m, 6H), 4.93 (dd, J$_1$=3.30 Hz, J$_2$=9.62 Hz, 1H), 4.57 (d, J=5.24 Hz, 2H), 4.00–3.20 (m, 95H), 3.24–3.05 (m, 6H); $^{13}$C NMR δ 166.3, 133.0, 132.5, 123.2, 118.6, 114.7, 99.5, 99.4, 99.2, 98.4, 82.5, 82.3, 82.0, 81.0, 80.9, 80.5, 80.0, 79.0, 74.4, 72.0, 71.8, 71.5, 71.3, 69.3, 62.0, 61.8, 61.6, 61.5, 59.4, 59.1, 59.0, 58.8. Anal. Calcd for C$_{72}$H$_{118}$O$_{37}$: C, 54.88; H, 7.55. Found: C, 55.13; H, 7.63.

EXAMPLE 33

$2^A$-O-[p-(tert-Butyl)benzoyl]heptakis(3,6-di-O-methyl)-$2^B,2^C,2^D,2^E,2^F,2^G$-hexa-O-methyl-β-cyclodextrin A permethylated monoalkenyl-β-cyclodextrin was prepared as in Example 27 from 1.00 g (0.68 mmol) of $2^A$-O-[p-(tert-butyl)benzoyl]heptakis(3-O-methyl)-$2^B,2^C,2^D,2^E,2^F,2^G$-hexa-O-methyl-β-cyclodextrin, 1.94 g (9.46 mmol) of 2,6-di(tert-butyl)-4-methylpyridine and 1.17 g (7.10 mmol) of methyl triflate to give 0.88 g (82% yield) of $2^A$-O-[p-(tert-butyl)benzoyl]heptakis(3,6-di-O-methyl)-$2^B,2^C,2^D,2^E,2^F,2^G$-hexa-O-methyl-β-cyclodextrin; m 132°–134° C.; $[\alpha]_D^{25}$ +142°–7° (C, 1.52, CHCl$_3$); $^1$H NMR δ 8.10 (d, J=8.71 Hz, 2H), 7.43 (d, J=8.71 Hz, 2H), 5.34 (d, J=3.31 Hz, 1H), 5.22–5.08 (m, 6H), 5.00 (dd, J$_1$=3.31 Hz, J$_2$=9.64 Hz, 1H), 4.03–3.30 (m, 95H), 3.26–3.06 (m, 6H), 1.35 (s, 9H); $^{13}$C NMR δ 166.6, 130.3, 127.8, 125.7, 99.5, 99.4, 99.1, 98.2, 82.5, 82.2, 82.1, 81.9, 81.2, 80.9, 80.8, 80.5, 79.9, 79.0, 77.6, 74.5, 71.8, 71.4, 71.3, 62.0, 61.8, 61.6, 61.5, 59.4, 59.1, 59.0, 58.9, 35.5, 31.6. Anal. Calcd for C$_{73}$H$_{122}$O$_{36}$: C, 55.64; H, 7.80. Found: C, 55.45; H, 7.75.

EXAMPLE 34

Heptakis(3,6-di-O-methyl)-$2^B,2^C,2^D,2^E,2^F,2^G$-hexa-O-methyl-β-cyclodextrin The cyclodextrin of Example 33 was stable in a hot solution of LiOH in THF-ethanol-water, but was reduced with LiAlH$_4$ in ethyl ether to give the monoalcohol as follows.

A solution of the cyclodextrin of Example 33 (0.50 g, 0.32 mmol) in ether (7 mL) was refluxed with LiAlH$_4$ (0.058 g, 1.53 mmol) for 24 h. Moist ether was added to decompose the excess LiAlH$_4$ and the mixture was concentrated. The residue was partitioned between CHCl$_3$ and water, and the organic layer was separated and washed with water 2 more times. After being dried and concentrated, the residue was subjected to column chromatography (CHCl$_3$:CH$_3$OH/80:1) to give 0.39 g (87% yield) of heptakis(3,6-di-O-methyl)-$2^B,2^C,2^D,2^E,2^F,2^G$-hexa-O-methyl-β-cyclodextrin; mp 105°–107° C.; $[\alpha]_D^{25}$ +145.0° (c, 0.36, CHCl$_3$): $^1$H NMR δ 5.20–5.06 (m, 6H), 4.89 (d, J=3.27 Hz, 1H), 4.34 (d, J=7.13 Hz, 1H, OH), 3.95–3.31 (m, 96 H), 3.27–3.10 (m, 6H); $^{13}$C NMR δ 102.4, 100.1, 99.9, 99.8, 99.6, 99.3, 99.1, 84.5, 83.4, 82.9, 82.6, 82.5, 82.4, 82.2, 81.6, 81.3, 81.2, 81.1, 80.7, 80.5, 79.1, 74.6, 72.3, 72.0, 71.8, 71.4, 71.3, 70.7, 62.4, 61.9, 61.8, 61.7, 61.3, 59.5, 59.3, 59.2, 59.0, 58.8, 58.7. Anal. Calcd for C$_{62}$H$_{110}$O$_{35}$: C, 52.61; H, 7.83. Found: C, 52.62; H, 8.00.

EXAMPLE 35

$2^A$-O-(p-Allyloxybenzyl)heptakis(3,6-di-O-methyl)-$2^B,2^C,2^D,2^E,2^F,2^G$-hexa-O-methyl-β-cyclodextrin The compound of Example 34 was converted to a permethylated $2^A$-O-(p-allyloxy)benzyl-β-cyclodextrin in a 64% yield by treatment with NaH and (p-allyloxy)benzyl chloride in DMF as follows.

Heptakis (3,6-di-O-methyl)-$2^B,2^C,2^D,2^E,2^F,2^G$-hexa-O-methyl-β-cyclodextrin (0.24 g, 0.17 mmol) in 5 mL of DMF was treated with NaH (0.041 g, 1.7 mmol) at room temperature for 2 h, and then 0.31 g (1.7 mmol) of p-allyloxybenzyl chloride was added. The mixture was stirred at rt for 24 h, and CH$_3$OH was added to decompose the excess NaH. The solvent was removed under reduced pressure to produce a slurry which was partitioned between CHCl$_3$ and water. The organic layer was separated, and washed with water. After being dried and concentrated, the crude product was chromatographed (CHCl$_3$: CH$_3$OH/80:1) to give 0.17 g (64% yield) of 2$^A$-O-(p-allyloxybenzyl)heptakis(3,6-di-O-methyl) -2$^B$,2$^C$,2$^D$,2$^E$,2$^F$,2$^G$-hexa-O-methyl-$\beta$-cyclodextrin; mp 100°–102° C.; [$\alpha$]$_D^{25}$+136.3° (c, 0.60, CHCl$_3$); $^1$H NMR $\delta$ 7.33 (d, J=8.83 Hz, 2H), 6.85 (d, J=8.83 Hz, 2H), 6.05 (m, 1H), 5.32 (m, 2H), 5.20–5.05 (m, 6H), 4.93 (d, J=3.31 Hz, 1H), 4.64 (s, 2H), 4.51 (d, J=5.27 Hz, 2H), 3.94–3.26 (m, 95H), 3.19 (dd, J$_1$=3.31 Hz, J$_2$=9.65 Hz, 7H); $^{13}$C NMR $\delta$ 133.8, 131.9, 131.5, 129.8, 118.0, 114.9, 114.8, 99.8, 99.4, 82.5, 82.3, 82.2, 80.9, 80.8, 80.6, 80.4, 80.0, 72.7, 72.1, 72.0, 71.8, 71.7, 71.6, 71.4, 71.3, 69.6, 69.3, 62.0, 61.9, 59.4, 59.1, 59.0, 58.9. Anal. Calcd for C$_{72}$H$_{120}$O$_{36}$: C, 55.37; H, 7.75. Found: C, 55.15; H, 7.84.

EXAMPLE 36

Preparation of Polyhydromethylsiloxane Copolymers

Polyhydromethylsiloxane copolymers were prepared by copolymerizing 10 parts of the cyclic tetramer of dimethylsiloxane and 1 part of the cyclic tetramer of hydromethylsiloxane according to the procedure of Bayona, J. M., et al., *Int. J. Environ. Anal. Chem.* 1987, 28, 263.

Polyhydromethylsiloxane Copolymer A

A mixture of 2.97 g (10 mmol) of 1,1,3,3,5,5,7,7-octamethylcyclotetrasiloxane (D$_4$), 0.24 g (1 mmol) of 1,3,5,7-tetramethylcyclotetrasiloxane (D'$_4$) and 45 $\mu$L (0.035 mg, 2×10$^{-4}$ mmol) of hexamethyldisiloxane was stirred with 4 mg of triflic acid in a 50-mL Teflon centrifuge tube for 50 h at room temperature in a reaction was similar to that reported by Bayona et al., supra. The mixture was neutralized with 30 mg of hexamethyldisilazane while being stirred for 5 min. The resulting polymer (MW about 15,000) was dissolved in 10 mL of CH$_2$Cl$_2$, the polymer was precipitated by adding 30 mL of CH$_3$OH, the mixture was centrifuged, and the solvent was decanted. The polymer was again dissolved in CH$_2$Cl$_2$ and precipitated by CH$_3$OH for a total of four more times. The polymer was then dried for 10 h under reduced pressure.

The molecular weight of the polyhydromethylsiloxane copolymer was determined by the amount of hexamethyldisiloxane, the endcapping agent, used in the reaction. By these reactions, the relative amounts of substituent cyclodextrin and the octyl group as well as the molecular weights of the resulting polymers can be determined.

Polyhydromethylsiloxane Copolymer B

A hydromethylpolysiloxane was specially prepared having tolyl substituents which have been found to be excellent crosslinking agents in polysiloxane systems according to Richter, et al., *J. Chromatogr.* 1983, 279, 21.

A mixture of 1.64 g (5.50 mmol) of 1,1,3,3,5,5,7,7-octamethylcyclotetrasiloxane (D4), 0.13 g (0.56 mmol) of 1,3,5,7-tetramethylcyclotetrasiloxane (D'$_4$), 0.24 g (0.89 mmol) of dimethoxyditolylsilane and 0.022 g (0.13 mmol) of hexamethyldisiloxane was stirred with 4 mg of triflic acid in a 50-mL Teflon centrifuge tube at room temperature for 50 h. This reaction was similar to that reported by Bayona et al., supra. This mixture was neutralized with 30 mg of hexamethyldisilazane while being stirred for 5 min. The resulting polymer (MW about 15,000) was dissolved in 10 mL of CH$_2$Cl and then precipitated by adding 30 mL of CH$_3$OH. The mixture was centrifuged, and the solvent was decanted. The polymer was again dissolved in CH$_2$Cl$_2$ and precipitated by CH$_3$OH for a total of four more times, and then dried under vacuum for 10 h.

Preparation of Formula I Cyclodextrin Polymethylsiloxane Polymers

Persubstituted $\beta$-cyclodextrin-bound polymethylsiloxanes of Formula I were synthesized by the hydrosilylation of the cyclodextrins of Examples 3, 4, 7, 9, 10, 11, 16 and 19 with polyhydromethylsiloxane Copolymer A or B of Example 36 in a manner similar to that previously reported by Bradshaw, J. S., et al., *J. Chromatogr.* 1987, 405, 169. Equimolar ratios of cyclodextrin to Si-H were used in the hydrosilylation reaction.

When using Copolymer A an excess of 1-octene was reacted in a second step following reaction with the cyclodextrin so that all Si-H units were reacted. Therefore, with reference to Formulas I or II, when Copolymer A is used, d is 1, e is O and the R$^2$ group is an octyl group. Assuming that all alkene-substituted cyclodextrin reacted with the polyhydromethylsiloxane copolymer, the resulting polymer would have a ratio of 50 dimethylsiloxanes (i.e. b is 50) to 4 methylcyclodextrin-substituted siloxanes (i.e. c is 4) to 1 methyloctylsiloxane (i.e. d is 1) and a is about 3.8.

When synthesizing Copolymer B a ditolylsilyl group was built into the polymer to enhance crosslinking capabilities. Therefore, with references to Formulas I and II, when Copolymer B is used, d is O, e is 2 and the R$^3$ group is tolyl. Again, assuming that all alkene-substituted cyclodextrin reacted with the polyhydromethylsiloxane copolymer, the resulting polymer would have a ratio of 50 dimethylsiloxanes (i.e. b is 50) to 5 methylcyclodextrin-substituted siloxanes (i.e. c is 5) to 2 ditolylsiloxanes (i.e. e is 2) and a is about 3.33.

EXAMPLE 37

General Procedure for the Preparation of $\beta$-Cyclodextrin-containing Methylpolysiloxanes of Formula I A representative synthetic procedure is given for preparing a cyclodextrin attached via a single attachment arm to a polysiloxane copolymer backbone using the 6$^A$-O-(p-allyloxyphenyl)heptakis(2,3-di-O-methyl)-2$^B$,2$^C$,2$^D$,2$^E$,2$^F$,2$^G$-hexa-O-methyl-$\beta$-cyclodextrin of Example 3 and the polyhydromethylsiloxane Copolymer A of Example 36. The procedure was carried out in the following manner. The cyclodextrin (0.12 g, 0.08 mmol), hydromethylpolysiloxane Copolymer A (0.08 g, 0.1 mmol of Si-H)[14] and 3 g of toluene were placed in a 50-mL Teflon centrifuge tube. Parafilm was placed around the cap to keep out moisture. The mixture was heated in an oil bath at 85°–90° C. for 1 h. Then 40 $\mu$L of 1% H$_2$PtCl$_6$ (in THF-ethanol) was added. The mixture was stirred at 85°–90° C. for 72 h. After 1 g of 1-octene was added, the reaction mixture was stirred overnight at 85°–90° C. The solvent was evaporated. The residue was dissolved in 10 mL of CH$_2$Cl$_2$, followed by 10 mL of CH$_3$OH and 10 mL of water. The mixture was centrifuged and the water-CH$_3$OH layer was removed. This process was repeated three more times. The CH$_2$Cl$_2$ was evaporated and the residue was dried under vacuum for 10 h at 60° C. to give 0.17 g (82%) Of a cyclodextrin polysiloxane polymer. The proton NMR spectrum of the resulting polymer was consistant with the structure shown in Formula I where p is 1, Q is $CH_2$—O—p—$C_6H_4$—$OCH_2$, n is 6, R is $CH_2OCH_3$, m is 14, $R^1$ is $CH_3$, e is 0, d is 1, $R^2$ is octyl, b is 50, c is 4 and a is 3.8.

EXAMPLE 38

Following the procedure of Example 37 the $6^A$-O-(p-allyloxyphenyl)heptakis(2,3-di-O-methyl)-$6^B,6^C,6^D,6^E,6^F,6^G$-hexa-O-acetyl-$\beta$-cyclodextrin of Example 4 was reacted with the hydromethylpolysiloxane Copolymer A of Example 36 to provide a cyclodextrin polysiloxane polymer having the structure shown in Formula I where p is 1, Q is $CH_2O$—p—$C_6H_4$—$OCH_2$, n is 6, R is $CH_2OC(O)CH_3$, m is 14, $R^1$ is $CH_3$, e is 0, d is 1, $R^2$ is octyl, b is 50, c is 4 and a is 3.8.

EXAMPLE 39

Following the procedure of Example 37 the $6^A$-O-(p-allyloxyphenyl)heptakis(2,3-di-O-methyl)-$6^B,6^C,6^D,6^E,6^F,6^G$-hexadeoxy-$\beta$-cyclodextrin of Example 7 was reacted with the hydromethylpolysiloxane Copolymer A of Example 36 to provide a cyclodextrin polysiloxane polymer having the structure shown in Formula I where p is 1, Q is $CH_2O$—p—$C_6H_4$—$OCH_2$, n is 6, R is $CH_3$, m is 14, $R^1$ is $CH_3$, e is 0, d is 1, $R^2$ is octyl, b is 50, c is 4 and a is 3.8.

EXAMPLE 40

Following the procedure of Example 37 the $6^A$-allyl-$6^A$-deoxyheptakis(2,3-di-O-methyl)-$6^B,6^C,6^D,6^E,6^F,6^G$-hexa-O-methyl-$\beta$-cyclodextrin of Example 9 was reacted with the hydromethylpolysiloxane Copolymer A of Example 36 to provide a cyclodextrin polysiloxane polymer having the structure shown in Formula I where p is 1, Q is $CH_2CH_2$, n is 6, R is $CH_2OCH_3$, m is 14, $R^1$ is $CH_3$, e is 0, d is 1, $R^2$ is octyl, b is 50, c is 4 and a is 3.8.

EXAMPLE 41

Following the procedure of Example 37 the $6^A$-O-allylheptakis(2,3-di-O-methyl)-$6^B,6^C,6^D,6^E,6^F,6^G$-hexa-O-methyl-$\beta$-cyclodextrin of Example 10 was reacted with the hydromethylpolysiloxane Copolymer A of Example 36 to provide a cyclodextrin polysiloxane polymer having the structure shown in Formula I where p is 1, Q is $CH_2OCH_2$, n is 6, R is $CH_2OCH_3$, m is 14, $R^1$ is $CH_3$, e is 0, d is 1, $R^2$ is octyl, b is 50, c is 4 and a is 3.8.

EXAMPLE 42

Following the procedure of Example 37 the heptakis(2,3-di-O-methyl)-$6^B,6^C,6^D,6^E,6^F,6^G$-hexa-O-methyl-$6^A$-O-$\omega$-undecylenyl-$\beta$-cyclodextrin of Example 11 was reacted with the hydromethylpolysiloxane Copolymer A of Example 36 to provide a cyclodextrin polysiloxane polymer having the structure shown in Formula I where p is 1, Q is $CH_2O(CH_2)_8CH_2$, n is 6, R is $CH_2OCH_3$, m is 14, $R^1$ is $CH_3$, e is 0, d is 1, $R^2$ is octyl, b is 50, c is 4 and a is 3.8.

EXAMPLE 43

Following the procedure of Example 37 the $6^A$-deoxyheptakis (2,3-di-O-methyl)-$6^B,6^C,6^D,6^E,6^F$,6G-hexa-O-methyl-$6^A$-methylene-$\delta$-cyclodextrin of Example 16 was reacted with the hydromethylpolysiloxane Copolymer A of Example 36 to provide a cyclodextrin polysiloxane polymer having the structure shown in Formula I where p is 0, n is 6, $R^1$ is $CH_2OCH_3$, m is 14, $R^1$ is $CH_3$, e is 0, d is 1, $R^2$ is octyl, b is 50, c is 4 and a is 3.8.

EXAMPLE 44

Following the procedure of similar to that of Example 37 the $6^A$-[p-allyloxy)benzamido]-$6^A$-deoxyheptakis(2,3-di-O-methyl)-$6^B,6^C,6^D,6^E,6^F,6^G$-hexa-O-methyl-$\delta$-cyclodextrin of Example 19 was reacted with a ditolylsilyl containing hydromethylpolysiloxane Copolymer B of Example 36 to provide a cyclodextrin polysiloxane polymer having the structure shown in Formula I where p is 1, Q is $CH_2O$—p—$C_6H_4$—C(O)$NHCH_2$, n is 6, R is $CH_2OCH_3$, m is 14, $R^1$ is $CH_3$, e is 2, d is 0, $R^3$ is tolyl, b is 50, c is 5 and a is 3.33.

Other polymers can be prepared in a like manner.
Preparation of Formula II Cyclodextrin Polymethylsiloxane Polymers Persubstituted $\beta$-cyclodextrin-bound polymethylsiloxanes were synthesized by the hydrosilylation of the cycldextrins of Examples 22, 27, 32 and 35 onto Copolymer B of Example 37 in a manner similar to that used to prepard Formula II polymers reported above. Equimolar amounts of cyclodextrin and Si-H functional groups on the polymer were used in the hydrosilylation reaction.

EXAMPLE 45

General Procedure for the Preparation of $\beta$-Cyclodextrin-containing Methylpolysiloxanes of Formula II A representative synthetic procedure is given for preparing a cyclodextrin attached at the 3 position via a single attachment arm to a polysiloxane copolymer backbone using the $3^A$-O-(p-allyloxybenzoyl)heptakis(2,6-di-O-methyl)-$3^B,3^C,3^D,3^E,3^F,3^G$-hexa-O-methyl-$\beta$-cyclodextrin of Example 22 and the polyhydromethylsiloxane Copolymer B of Example 36. The procedure was carried out in the following manner.

The cyclodextrin (0.15 g, 0.094 mmol), the hydromethylpolysiloxane Copolymer B (0,084 g, 0.094 mmol of Si-H) and 5 g of toluene were placed in a 50-mL Teflon centrifuge tube. Parafilm was placed around the cap to keep out moisture. The mixture was heated in an oil bath at 85°–90° C. for 72 h, and the solvent was evaporated. A solution of the residue in $CH_2Cl_2$ (10 mL) was washed with 10 mL of $CH_3OH$ and 10 mL of water. The mixture was centrifuged and the water-$CH_3OH$ layer was removed. This process was repeated three more times. The solvent was evaporated and the residue was dried under vacuum at 60° C. for 20 h to give 0.20 (84% yield) of the resulting cyclodextrin containing polymer. The proton NMR spectrum of the resulting polymer was consistant with the structure shown in Formula II where p is 1, X' is O, Q' is C(O)—p— $C_6H_4$—$OCH_2$, n is 7, R is $CH_2OCH_3$, m is 13, $R^1$ is $CH_3$, e is 2, d is 0, $R^3$ is tolyl, b is 50, c is 5 and a is 3.33.

EXAMPLE 46

Following the procedure of Example 45 the $2^A$-O-(p-allyloxybenzoyl)heptakis(3-O-acetyl-6-O-methyl)-$2^B,2^C,2^D,2^E,2^F,2^G$-hexa-O-acetyl-$\beta$-cyclodextrin of Example 27 was reacted with the hydromethylpolysiloxane Copolymer B of Example 36 to provide a cyclodextrin polysiloxane polymer wherein the cyclodextrin is attached at the 2 position via a single attachment arm to the polysiloxane copolymer backbone and having the structure shown in Formula II where p is 1, X' is O, Q' is C(O)—p—$C_6H_4$—$OCH_2$, n is 7, R is $CH_2OCH_2$, m is 13, $R^1$ is C(O)$CH_3$, e is 2, d is 0, $R^3$ is tolyl, b is 50, c is 5 and a is 3.33.

EXAMPLE 47

Following the procedure of Example 45 the $2^A$-O-(p-allyloxybenzoyl)heptakis(3,6-di-O-methyl)-$2^B,2^C,2^D,2^E,2^F,2^G$-hexa-O-methyl-$\beta$-cyclodextrin of Example 32 was reacted with the hydromethylpolysiloxane Copolymer B of Example 36 to provide a cyclodextrin polysiloxane polymer wherein the cyclodextrin is attached at the 2 position via a single attachment arm to the polysiloxane copolymer backbone and having the structure shown in Formula II where p is 1, X' is O, Q' is C(O)—p—$C_6H_4$—$OCH_2$, n is 7, R is $CH_2OCH_3$, m is 13, $R^1$ is $CH_3$, e is 2, d is 0, $R^3$ is tolyl, b is 50, c is 5 and a is 3.33.

EXAMPLE 48

Following the procedure of Example 45 the $2^A$-O-(p-allyloxybenzyl)heptakis(3,6-di-O-methyl)-$2^B,2^C,2^D,2^E,2^F,2^G$-hexa-O-methyl-$\beta$-cyclodextrin of Example 35 was reacted with the hydromethylpolysiloxane Copolymer B of Example 36 to provide a cyclodextrin polysiloxane polymer wherein the cyclodextrin is attached at the 2 position via a single attachment arm to the polysiloxane copolymer backbone and having the structure shown in Formula II where p is 1, X' is O, Q' is $CH_2$—p—$C_6H_4$—$OCH_2$, n is 7, R is $CH_2OCH_3$, m is 13, $R^1$ is $CH_3$, e is 2, d is 0, $R^3$ is tolyl, b is 50, c is 5 and a is 3.33.

Preparation of Chiral Stationary Phases
Preparation of capillary columns

GC and SFC columns, 250 and 50 $\mu$m i.d., respectively, were prepared using cyano-deactivated fused silica capillaries, e.g. see Markides, et al., *J. High Resolut. Chromatogr./Chromatogr. Commun.* 1985, 8, 741. The static coating technique as disclosed by Bouche, et al., J. Gas Chromatogr. 1968, 6, 501, was employed for column preparation. Mixtures of $CH_2Cl_2$/n—$C_5h_{12}$ were used as solvents for the cyclodextrin polysiloxane polymer. The coating bath temperature was set at 40° C. After coating with the cyclodextrin polysiloxane polymer, the columns were purged with nitrogen for 40 min and then cross-linked using azo-t-butane as a free radical initiator as taught by Richter, et al., *J. High Resolut. Chromatogr./Chromatogr. Commun.* 1983, 6, 371. The columns were thermally treated by temperature programming from 40° C. to 220° C., at a rate of 4° C. min$^{-1}$, holding at the final temperature for 30 min. The columns were then rinsed with the coating solvent (1 mL for a GC column, and 0.5 mL for an SFC column) and purged with nitrogen for 40 min. Finally, the columns were conditioned under helium purge by programming the temperature from 40° C. to 230° C. at a rate of 1° C. min$^{-1}$ with a holding time of 2 h at the final temperature.

Gas chromatography

GC experiments were performed on an HP Model 5890 gas chromatograph (Hewlett Packard, Avondale, Pa., USA) equipped with a flame ionization detector. Helium was used as the carrier gas. Split injection (200:1) was used. An HP Model 3392A recording integrator (Hewlett Packard) was used to record the solute retention times and peak areas.

Supercritical fluid chromatography

SFC experiments were conducted using a Lee Scientific Model 501 SFC system (Dionex, Sunnyvale, Calif., USA) equipped with a flame ionization detector. SFC grade $CO_2$ was used as the mobile phase. A helium actuated automatic Valco injector (Valco, Houston, Tex., USA) was used for sample introduction. Homemade integral type restrictors were used. Pressure programming was employed for SFC separations of the chiral solutes.

In addition or, as an alternative to, the placing of a coating on the inside surface of the chromatography column, the polymers may also be coated onto particles and used as a solid packing in the column. Such coated particles may be used as solid packing in supercritical fluid, liquid or gas chromatography columns.

Illustrations of Chiral Separations

The newly synthesized cyclodextrin-bound polysiloxanes described above were applied as stationary phases in GC and SFC, and were found to be highly efficient. In GC, for example, efficiency values of 2,500 to 3500 effective theoretical plates per meter were regularly obtained for most chiral solutes. The SFC column efficiencies were on the order of 4000–5000 plates per meter. The values for Formula I and Formula II polymers were comparable. These efficiency values are much higher than those recently reported by Schurig and coworkers (e.g. Schmalzing, et al., *J. High Resolut. Chromatogr.* 1992, 15, 723) who synthesized similar cyclodextrin stationary phases and measured efficiencies for over 100 chiral solutes. The efficiency values reported by those Schmalzing, et al ranged between 300 and 2,100 effective theoretical plates per meter. For more than 70% of the solutes, the efficiency values were below 1,500 effective plates per meter. In SFC, column efficiencies on the order of only 2000 theoretical plates per meter were reported by the above authors, indicating that the SFC column efficiency was barely half of that achieved by the present invention for both Forula I and II products.

Both in GC and SFC, the cyclodextrin-bonded stationary phases described in in the above examples demonstrate excellent selectivities for a wide variety of chiral solutes of various chemical classes.

EXAMPLE 49

The GC separation of mandelic acid methyl ester enantiomers on the $\beta$-cyclodextrin-bound polysiloxane phase of Example 37 was accomplished using a 30 meter fused silica column having a 250 $\mu$m inside diameter which was coated with a polymer film having a thickness of about 0.25 $\mu$m film thickness. The enantiomers were eluted at a temperature of 120° C. using helium as a carrier gas; detection was by FID. Baseline resolution was easily achieved. The chromatogram showing the separation is presented in FIG. 1.

EXAMPLE 50

Figure 2A:
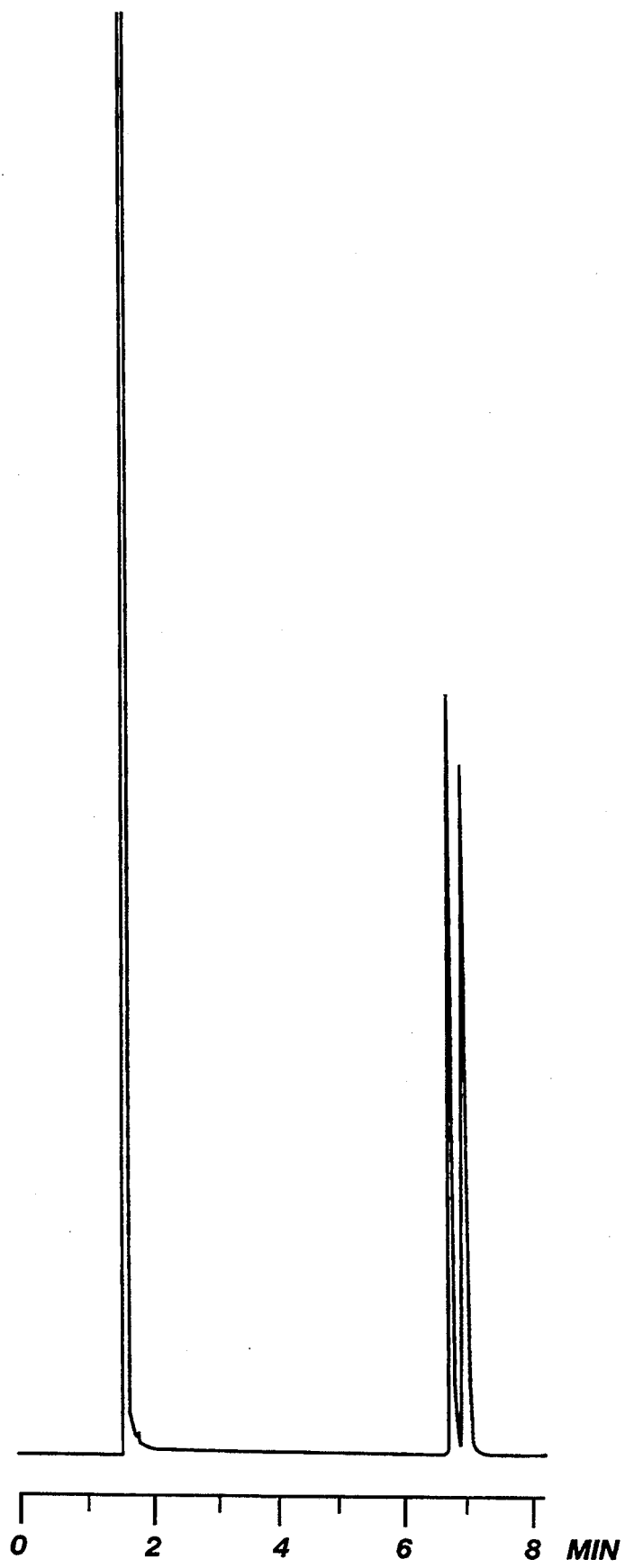
FIG. 2A. Shows the separation of (±)-trans-1,2-cyclohexanediol enantiomers on the β-cyclodextrin-bound polysiloxane phase shown in Example 23 by GC. Conditions: 30 m×250 μm i.d. column, 0.25 μm film thickness; 140° C.; helium carrier gas; FID.

The GC separation of ($\pm$)-trans-1,2-cyclohexanediol enantiomers using the $\beta$-cyclodextrin-bound polysiloxane polymer phase of Example 39 was carried out in a manner similar to that shown in Example 49 with the enantiomers being eluted at a temperature of 140° C. A chromatogram of the separation is shown in FIG. 2A.

Figure 2B:
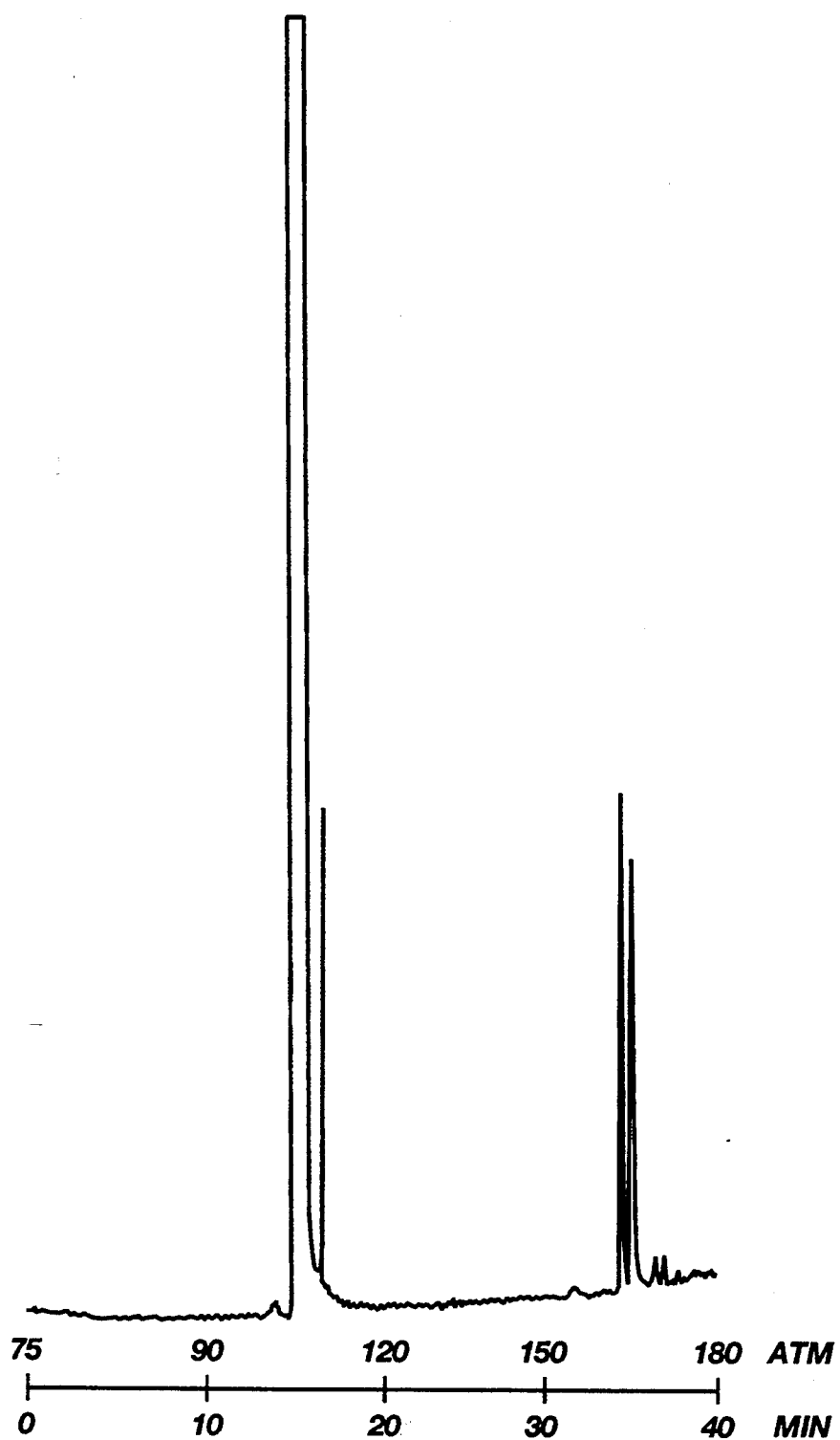
FIG. 2B. Shows the separation of (±)-trans-1,2-cyclohexanediol enantiomers on the β-cyclodextrin-bound polysiloxane phase shown in Example 23 by SFC. Conditions: 15 m×50 μm i.d. column, 0.20 μm film thickness; 60° C.; pressure program from 75 atm, 5 min hold, at a rate of 3 atm min$^{-1}$, to 180 atm.

The SFC separation of ($\pm$)-trans-1,2-cyclohexanediol enantiomers using the $\beta$-cyclodextrin-bound polysiloxane polymer phase of Example 39 was carried out using a 15 m $\times$ 50 $\mu$m i.d. fused silica column having a 0.20 $\mu$m cyclodextrin polysiloxane polymer film thickness. $CO_2$ was used as mobile phase at a temperature of 60° C. The pressure program varied from 75 atm, 5 min hold, at a rate of 3 atm min$^{-1}$, to 180 atm. A chromatogram of the separation is shown in FIG. 2B.

EXAMPLE 51

Figure 3:
FIG. 3. Shows the SFC separation of (±)-2,4-pentanediol enantiomers on the β-cyclodextrin-bound polysiloxane phase shown in Example 25. Conditions: 15 m ×50 μm i.d. column, 0.20 μm film thickness; 60° C.; pressure program from 75 atm, 5 min hold, at a rate of 3 atm min$^{-1}$, to 180 atm.

The SFC separation of (±)-2,4-pentanediol enantiomers using the β-cyclodextrin-bound polysiloxane polymer phase of Example 41 was carried out using the same conditions as shown for the SFC separation in Example 50. A chromatogram of the separation is shown in FIG. 3.

In spite of the high susceptibility of the diols toward adsorption, sharp peaks were obtained in both Examples 50 and 51, which is indicative of the inertness of the prepared columns.

EXAMPLE 52

Figure 4A:
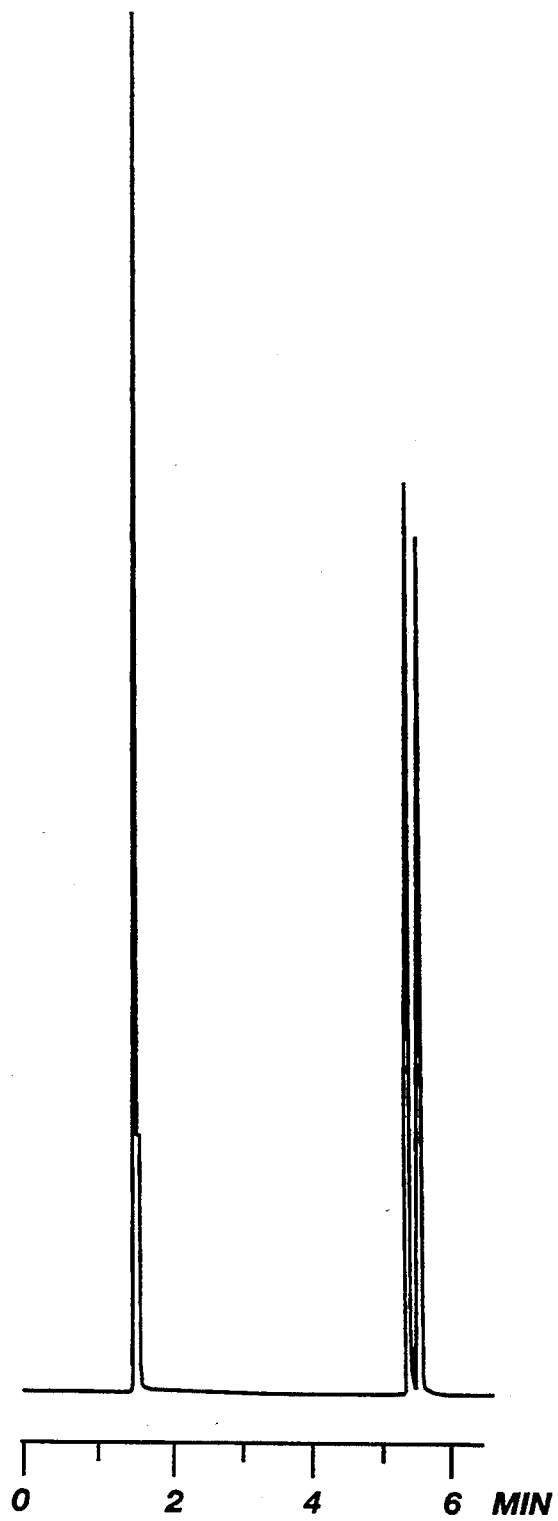
FIG. 4A. Shows the separation of (±)-α-(trifluoromethyl)benzyl alcohol enantiomers by GC on the β-cyclodextrin-bound polysiloxane phase shown in Example 26. Conditions: 30 m×250 μm i.d. fused silica column, 0.25 μm film thickness; 140° C.; helium carrier gas, FID.

The GC separation of (±)-α-(trifluoromethyl)benzyl alcohol enantiomers using the β-cyclodextrin-bound polysiloxane polymer phase of Example 42 was carried out in a manner similar to that shown in Example 50 with the enantiomers being eluted at a temperature of 140° C. A chromatogram of the separation is shown in FIG. 4A.

Figure 4B:
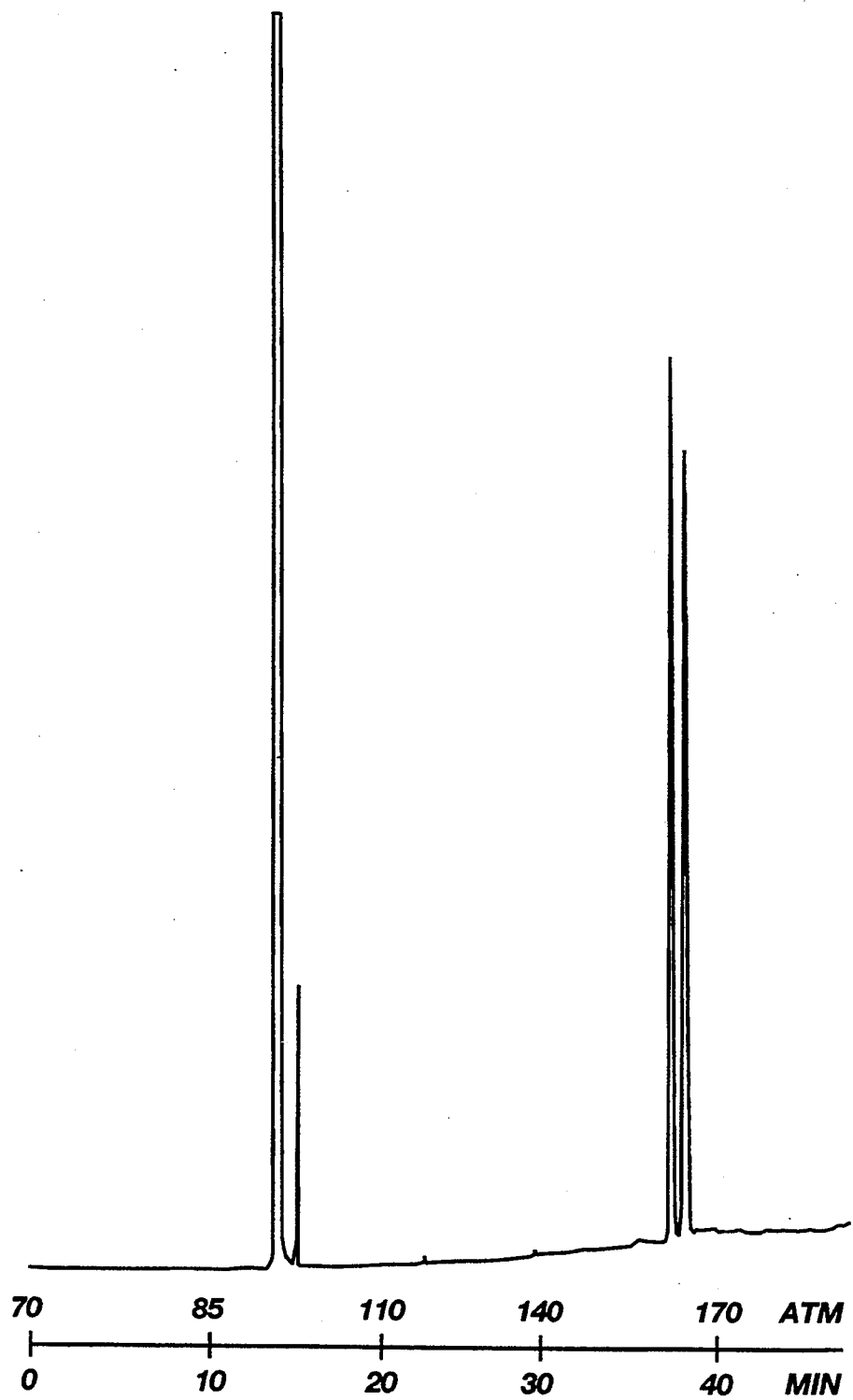
FIG. 4B. Shows the separation of (±)-α-(trifluoromethyl)benzyl alcohol enantiomers by SFC on the β-cyclodextrin-bound polysiloxane phase shown in Example 23. Conditions: 15 m×50 μm i.d. fused silica column, 0.20 μm film thickness; 60° C.; pressure program from 75 atm, 5 min hold, at a rate of 3 atm min$^{-1}$, to 200 atm.
Figure 5:
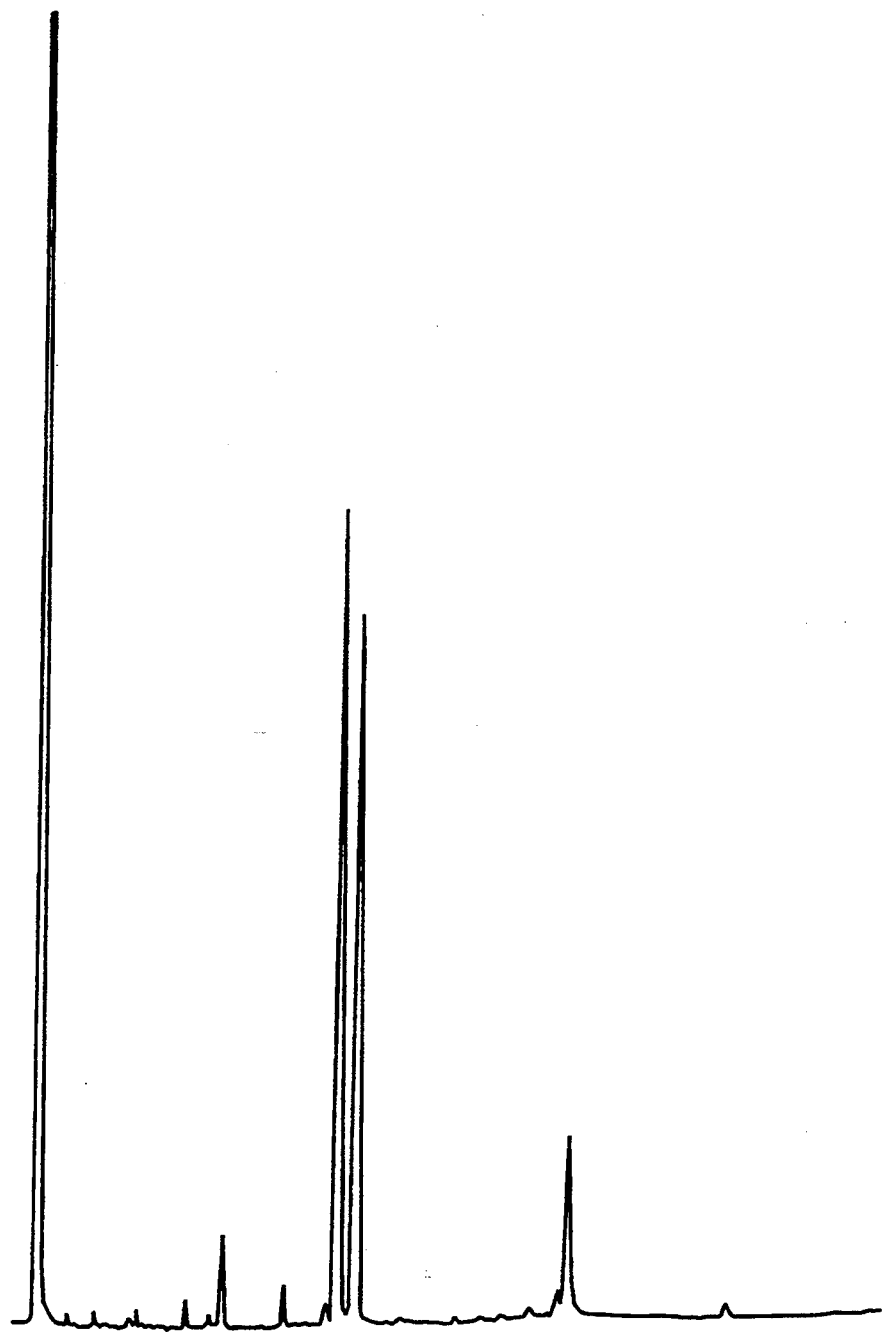
FIG. 5. Shows the separation of pantolactone enantiomers by SFC on the β-cyclodextrin-bound polysiloxane phase shown in Example 28. Conditions: 15 m×50 μm i.d. fused silica solumn, 0.20 film thickness; 80° C.; pressure program 70 atm, 5 min hold, at a rate of 3 atm min$^{-1}$, to 200 atm.

The SFC separation of (±)-α-(trifluoromethyl)benzyl alcohol enantiomers using the β-cyclodextrin-bound polysiloxane polymer phase of Example 39 was carried out using the same conditions as shown for the SFC separation in Example 50 except that the pressure program varied from 75 atm 5 min hold, at a rate of 3 atm min$^{-1}$, to 200 atm. A chromatogram of the separation is shown in FIG. 4B.

EXAMPLE 53

The SFC separation of pantolactone enantiomers using the β-cyclodextrin-bound polysiloxane phase of Example 44 was was carried out using the same conditions as shown for the SFC separation in Example 50 except that the temperature was 80° C. and the pressure program varied from; 70 atm, 5 min hold, at a rate of 3 atm min$^{-1}$, to 200 atm.

EXAMPLE 54

Figure 6A:
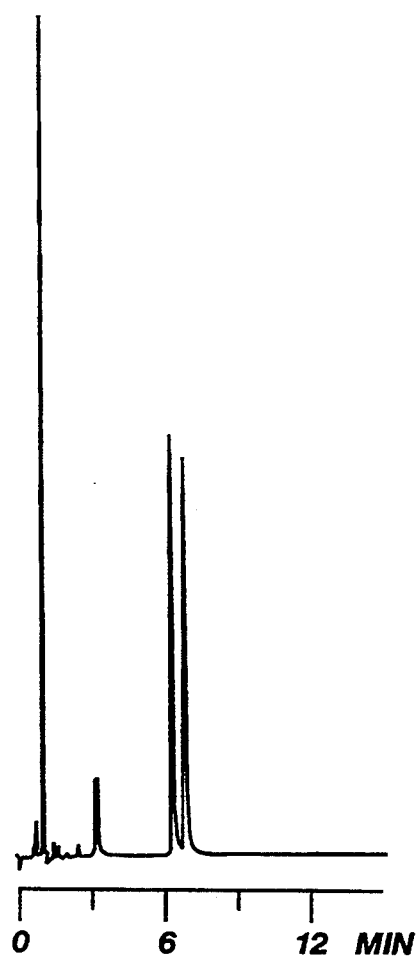
FIG. 6A. Shows the separation of pantolactone enantiomers by GC on the β-cyclodextrin-bound polysiloxane phase shown in Example 47. Conditions: 15 m×320 μm i.d. cyano-deactivated fused silica columns, 0.25 μm film thickness, 130° C. column temperature; helium carrier gas; split injection (100:1); FID.

The separation of pantolactone enantiomers by GC on the β-cyclodextrin-bound polysiloxane phase shown in Example 47 was accomplished using 15 meter by 320 μm i.d. cyano-deactivated fused silica columns. The inside was coated with a polymer film having a thickness of about 0.25 μm. The enantiomers were eluted at a column temperature of 130° C. using helium as a carrier gas. Other conditions were split injection (100:1). Detection was by FID. A chromatogram showing the separation is presented in FIG. 6A.

Figure 6B:
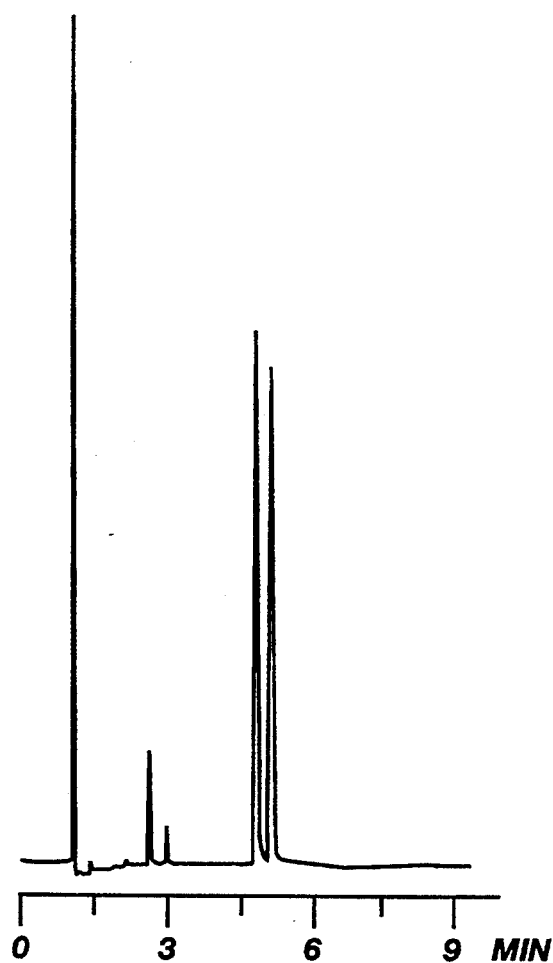
FIG. 6B. Shows the separation of pantolactone enantiomers by GC on the β-cyclodextrin-bound polysiloxane phase shown in Example 37. Conditions: 15 m×320 μm i.d. cyano-deactivated fused silica columns, 0.25 μm film thickness, 130° C. column temperature; helium carrier gas; split injection (100:1); FID.

The separation of pantolactone enantiomers by GC was carried out as in the preceding paragraph except that the β-cyclodextrin-bound polysiloxane phase shown in Example 37 was used. A chromatogram showing the separation is given in FIG. 6B.

This example illustrates comparable chiral selectivities when using the Formula I (Example 37) and Formula II (Example 47) polymers. Analogous results were obtained in SFC.

EXAMPLE 55

Figure 7A:
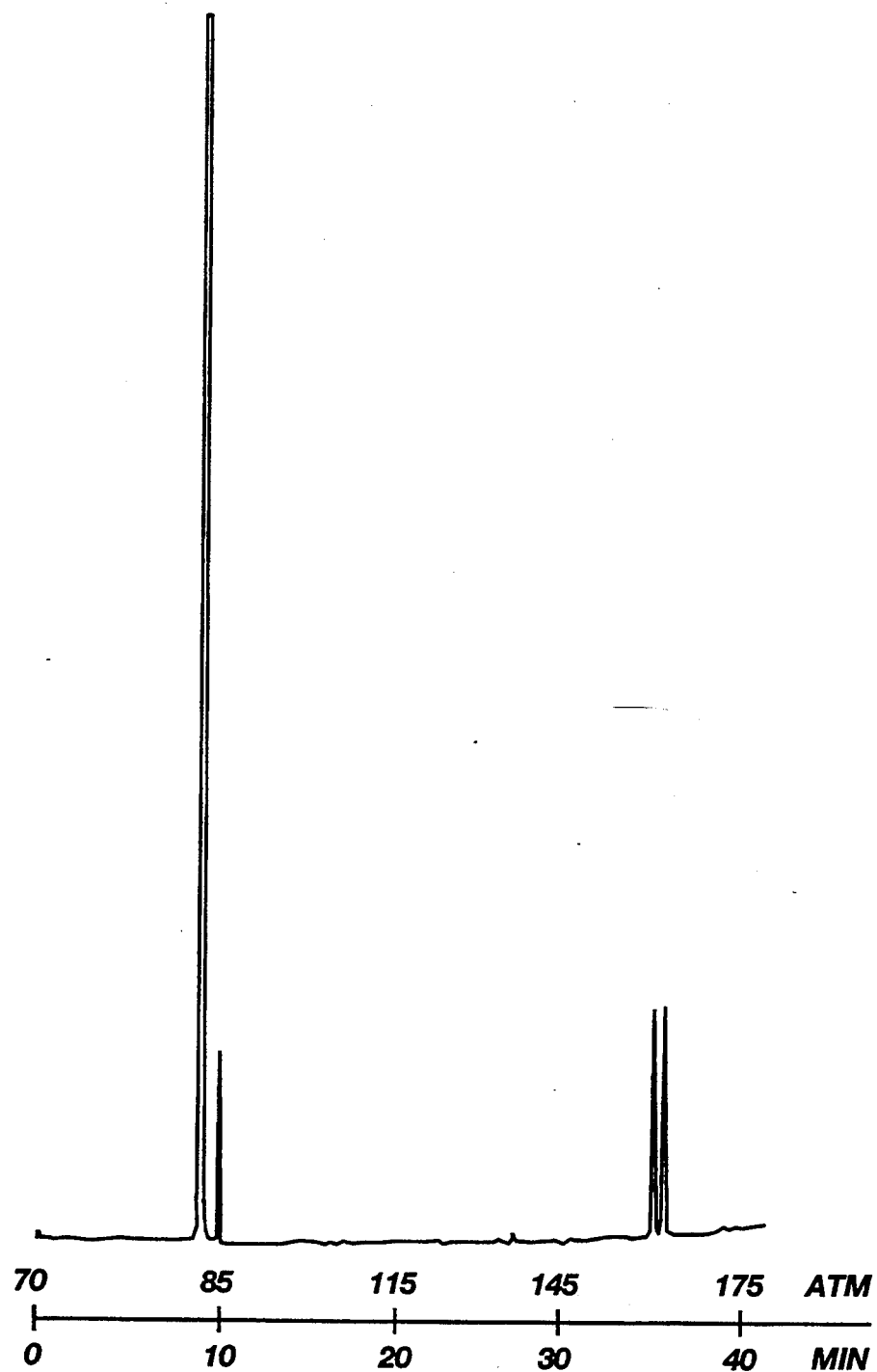
FIG. 7A. Shows the separation of t-2-phenyl-1-cyclohexanol enantiomers by SFC on the β-cyclodextrin-bound polysiloxane phase shown in Example 48. Conditions: 10 m×50 μm i.d. cyanode-activated fused silica solumn, 0.20 film thickness; 60° C. column temperature; pressure program from 70 atm, (5 min hold), at a rate of 3 atm min$^{-1}$, to 200 atm.; neat CO$_2$ mobile phase, timed-split injection; FID.

The SFC separation of t-2-phenyl-1-cyclohexanol enantiomers using the β-cyclodextrin-bound polysiloxane phase shown in Example 48 was carried out using a 10 m × 50 μm i.d. cyano-deactivated fused silica column having a 0.20 cyclodextrin polysiloxane polymer film thickness. Neat $CO_2$ was used as the mobile phase at a column temperature of 60°. The pressure program varied from 75 atm, (5 min hold), at a rate of 3 atm min$^{-1}$, to 200 atm. A chromatogram of the separation is given in FIG. 7A.

Figure 7B:
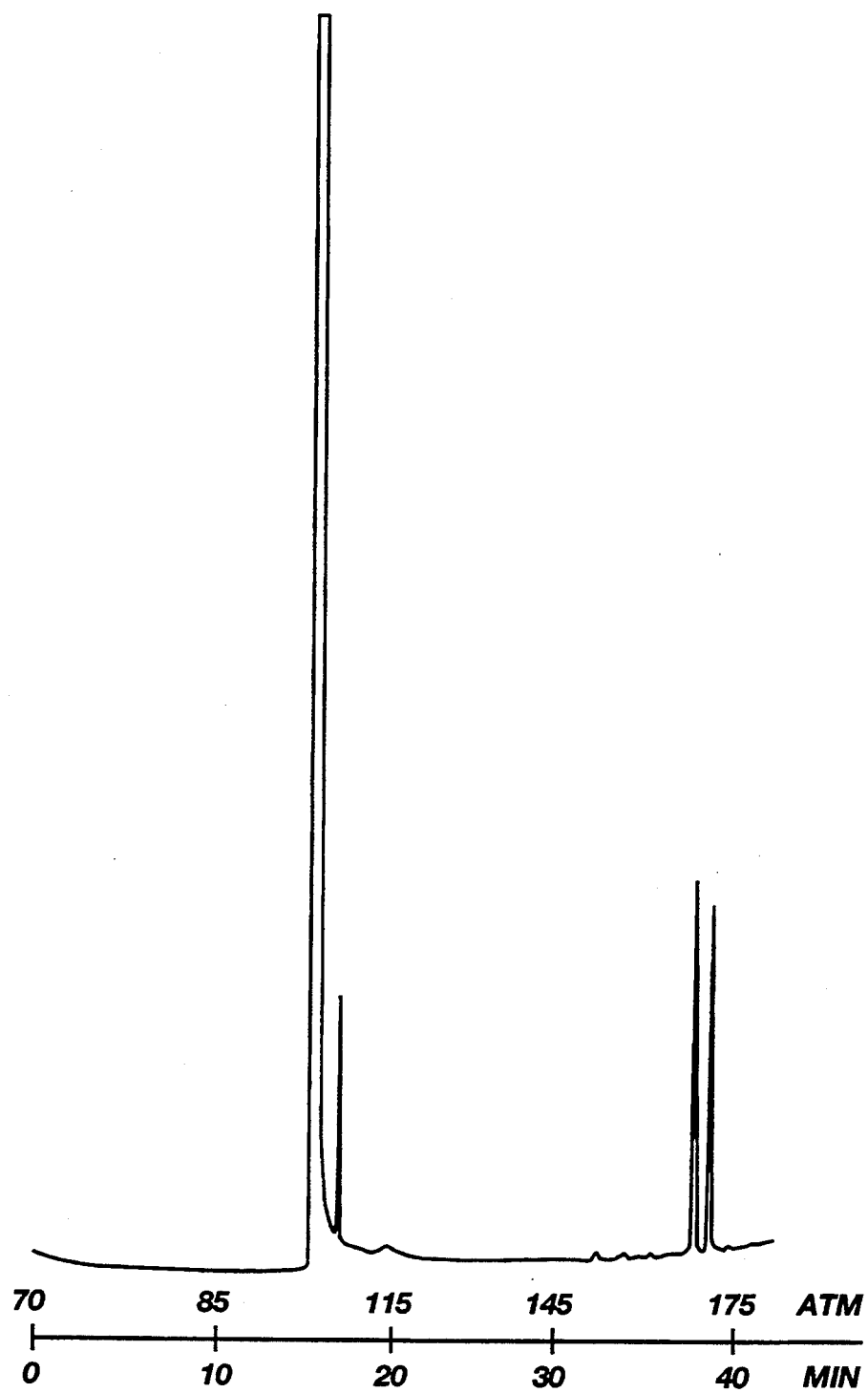
FIG. 7B. Shows the separation of t-2-phenyl-1-cyclohexanol enantiomers by SFC on the β-cyclodextrin-bound polysiloxane phase shown in Example 39. Conditions: 10 m×50 μm i.d. cyano-activated fused silica solumn, 0.20 film thickness; 60° C. column temperature; pressure program from 70 atm, (5 min hold), at a rate of 3 atm min$^{-1}$, to 200 atm.; neat CO$_2$ mobile phase, timed-split injection; FID.

The SFC separation of t-2-phenyl-1-cyclohexanol enantiomers was carried out as in the preceding paragraph using the β-cyclodextrin-bound polysiloxane phase shown in Example 39. A chromatogram of the separation is given in FIG. 7B.

This example illustrates comparable chiral selectivities when using the Formula I (Example 39) and Formula II (Example 48) polymers. Very similar performance in both efficiency and selectivity was obtained with both formula types.

EXAMPLE 56

Figure 8A:
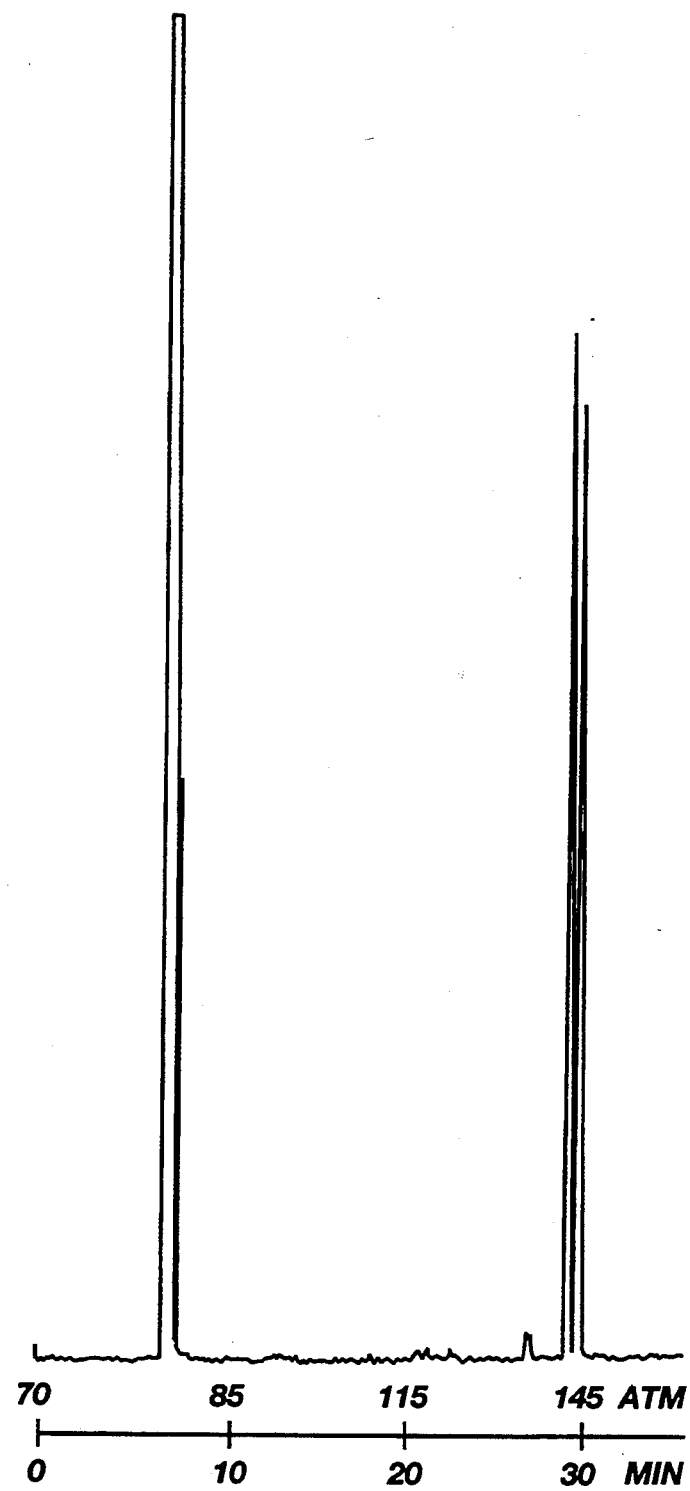
FIG. 8A. Shows the separation of τ-phenyl-τ-butyrolactone enantiomers by SFC on the β-cyclodextrin-bound polysiloxane phase shown in Example 45. Conditions: 10 m×50 μm i.d. cyano-deactivated fused silica solumn, 0.20 film thickness; 60° C. column temperature; pressure program from 70 atm, (5 min hold), at a rate of 3 atm min$^{-1}$, to 200 atm.; neat CO$_2$ mobile phase, timed-split injection; FID.

The SFC separation of τ-phenyl-τ-butyrolactone enantiomers using the β-cyclodextrin-bound polysiloxane phase shown in Example 45 was accomplished under conditions the same as in Example 55. A chromatogram of the separation is shown in FIG. 8A.

Figure 8B:
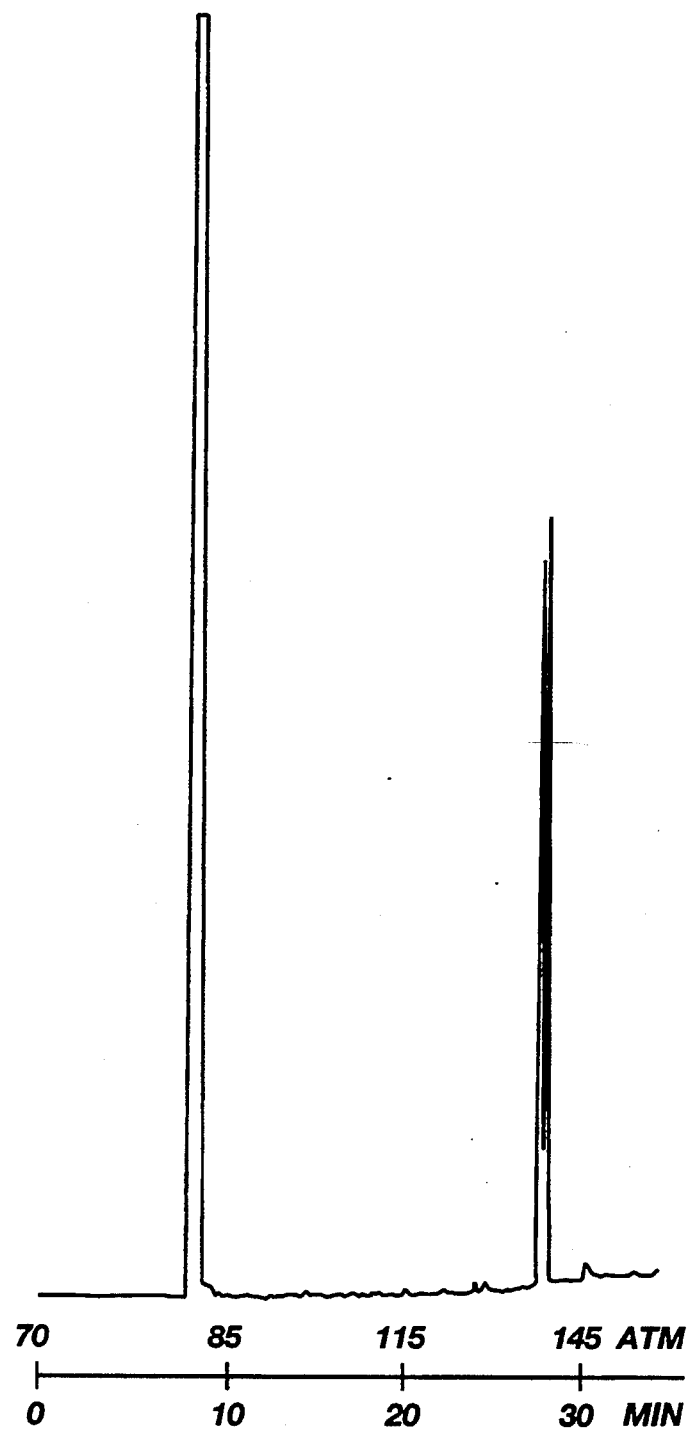
FIG. 8B. Shows the separation of τ-phenyl-τ-butyrolactone enantiomers by SFC on a copolymeric β-cyclodextrin-bound polysiloxane phase as disclosed in copending patent application Ser. No. 07/878,157 filed May 4, 1992. Conditions: 10 m×50 μm i.d. cyano-deactivated fused silica solumn, 0.20 film thickness; 60° C. column temperature; pressure program from 70 atm, (5 min hold), at a rate of 3 atm min$^{-1}$, to 200 atm.; neat CO$_2$ mobile phase, timed-split injection; FID.

The same SFC separation as in the above paragraph was carried out using a copolymeric β-cyclodextrin-bound polysiloxane phase as disclosed in copending patent application Ser. No. 07/878,157, filed May 4, 1992, U.S. Pat. No. 5,268,442. A chromatogram of the separation is shown in FIG. 8B.

All of the chromatograms presented are indicative of high separation efficiencies and excellent chiral selectivities of the newly synthesized stationary phases.

From the foregoing, it will be appreciated that the cyclodextrin polysiloxane polymers of the present invention provide stationary phases which achieve chromatographic separation of enantiomers with high chromatographic efficiency and selectivity. The cyclodextrin attached to the polysiloxane polymer backbone via a single attachment link have utility over a wide temperature range and with supercritical fluid mobile phases. It is therefore possible to utilize the inherent selectivity that the phase has at low temperature since the temperature can be chosen as an independent parameter in SFC in contrast to gas chromatography.

The present invention may be embodied in other specific forms without departing from its spirit or essential characteristics. The described embodiments are to be considered in all respects only as illustrative and not restrictive. The scope of the invention is, therefore, limited only by the appended claims rather than by the foregoing description. All changes which come within the meaning and range of functional equivalency of the claims are to be embraced within their scope.

We claim:

1. A cyclodextrin containing polymeric siloxane wherein the cyclodextrin is connected to the polymeric siloxane by a single linking member connected to the 6-position of the cyclodextrin and having the following general formula:

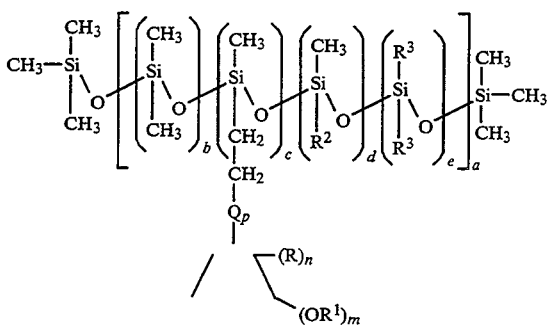

where n is an integer of 5 to 7, m is an integer of 12 to 16, p is 0 or 1, a is a numerical value of between about 1 to 10, b is an integer of 20 to 150, c is an integer of 1 to 20 with the proviso that the ratio of b to c is between 2:1 and 150:1, d is an integer of 0 to 5, e is an integer of 0 to 5, R is a member selected from the group consisting of $CH_3$, $CH_2OR^1$, $CH_2O(CH_2)_xOR^1$, $CH_2O$—Ar—O—$R^1$, $CH_2O(CH_2CH_2O)_xR^1$ and $CH_2OC(O)R^1$ where $R^1$ is a member selected from the group consisting of alkyl, aralkyl, aryl and alkaryl, Q is a member selected from the group consisting of $CH_2(CH_2)_x$, $(CH_2X(CH_2)_x$, $CH_2X$—$(CH_2)_x$—$XCH_2$, $CH_2X$—$(CH_2)_x$—$C(O)XCH_2$, $CH_2X$—$C(O)(CH_2)_x$—$XCH_2$, $CH_2X$—Ar—$XCH_2$, $CH_2X$—$(CH_2)_x$—Ar—$XCH_2$, $CH_2X$—Ar—$(CH_2)_x$—$XCH_2$, $CH_2X$—$(CH_2)_x$—Ar—$(CH_2)_x$—$XCH_2$, $CH_2X$—Ar—$C(O)XCH_2$, $CH_2X$—$(CH_2)_x$—Ar—$C(O)XCH_2$, $CH_2X$—Ar—$(CH_2)_x$—$C(O)XCH_2$, $CH_2X$—$(CH_2)_x$—Ar—$(CH_2)_x$—$C(O)XCH_2$, $CH_2XC(O)$—Ar—$XCH_2$, $CH_2XC(O)$—$(CH_2)_x$—Ar—$XCH_2$, $CH_2XC(O)$—Ar—$(CH_2)_x$—$XCH_2$ and $CH_2XC(O)$—$(CH_{2x}$—Ar—$(CH_{2x}$—$XCH_2$, x is an integer of between 1 and 10, X is a member selected from the group consisting of O, S, and $NR^4$ where $R^4$ is H or $R^1$, Ar and aryl are members selected from the group consisting of benzene, thiophene, furan, pyridine, pyrrole, imidazole, oxazole, thiazole, pyrazole, pyrimidine and cyclohexane rings and $R^2$ and $R^3$ are members selected from the group consisting of alkyl, aralkyl and alkaryl.

2. The polymer of claim 1 wherein n is 5 and m is 12.
3. The polymer of claim 1 wherein n is 7 and m is 16.
4. The polymer of claim 1 wherein n is 6 and m is 14.
5. The polymer of claim 4 wherein X is 0 with the proviso that when a XC(O) moiety is present X is a member selected from the group consisting of O and NH.
6. The polymer of claim 4 wherein Ar is phenylene.
7. The polymer of claim 4 wherein x is an integer of 1 to 5.
8. The polymer of claim 4 where p is 1, Q is $CH_2O$—p—$C_6H_4$—$OCH_2$, R is $CH_2OCH_3$, $R^1$ is $CH_3$, e is 0, d is 1, $R^2$ is octyl, b is 50 and c is 4.
9. The polymer of claim 4 where p is 1, Q is $CH_2O$—p—$C_6H_4$—$OCH_2$, R is $CH_2OC(O)CH_3$, $R^1$ is $CH_3$, e is 0, d is 1, $R^2$ is octyl, b is 50 and c is 4.
10. The polymer of claim 4 wherein p is 1, Q is $CH_2O$—p—$C_6H_4$—$OCH_2$, R is $CH_3$, $R^1$ is $CH_3$, e is 0, d is 1, $R^2$ is octyl, b is 50 and c is 4.
11. The polymer of claim 4 wherein p is 1, Q is $CH_2CH_2$, R is $CH_2OCH_3$, $R^1$ is $CH_3$, e is 0, d is 1, $R^2$ is octyl, b is 50 and c is 4.

12. The polymer of claim 4 wherein p is 1, Q is $CH_2OCH_2$, R is $CH_2OCH_3$, $R^1$ is $CH_3$, e is 0, d is 1, $R^2$ is octyl, b is 50 and c is 4.
13. The polymer of claim 4 wherein p is 1, Q is $CH_2O(CH_2)_8CH_2$, R is $CH_2OCH_3$, $R^1$ is $CH_3$, e is 0, d is 1, $R^2$ is octyl, b is 50 and c is 4.
14. The polymer of claim 4 wherein p is 0, R is $CH_2OCH_3$, $R^1$ is $CH_3$, e is 0, d is 1, $R^2$ is octyl, b is 50 and c is 4.
15. The polymer of claim 4 wherein p is 1, Q is $CH_2O$—p—$C_6H_4$—$C(O)NHCH_2$, R is $CH_2OCH_3$, $R^1$ is $CH_3$, e is 2, d is 0, $R^3$ is tolyl, b is and c is 5.
16. A cyclodextrin containing polymeric siloxane wherein the cyclodextrin is connected to the polymeric siloxane by a single linking member connected to the 2 or 3-position of the cyclodextrin and having the following general formula:

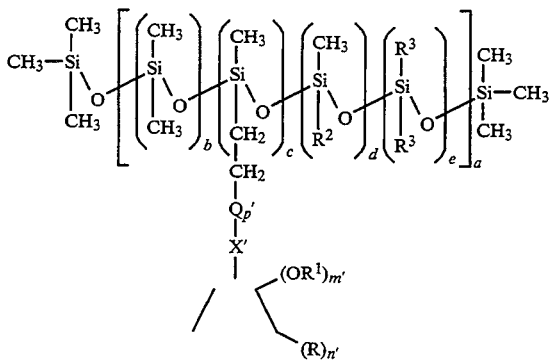

where n' is an integer of is an integer of 11 to 15, p is 0 or 1, a is a numerical value of between about 1 to 10, b is an integer of 20 to 150, c is an integer of 1 to 20 with the proviso that the ratio of b to c is between 2:3, and 150:1, d is an integer of 0 to 5, e is an *integer of 0 to 5, R is a member selected from the group consisting of $CH_3$, $CH_2OR^1$, $CH_2O(CH_2)_xOR^1$, $CH_2O$—Ar—O—$R^1$, $CH_2O(CH_2CH_2O)_xR^1$ and $CH_2OC(O)R^1$ where $R^1$ is a member selected from the group consisting of alkyl, aralkyl, aryl and alkaryl, Q' is a member selected from the group consisting of $CH_2(CH_2)_x$, $(CH_2)_x$—$XCH_2$, $(CH_2)_x$—$C(O)XCH_2$, $C(O)(CH_2)_x$—$XCH_2$, Ar—$XCH_2$, $(CH_2)_x$—Ar—$XCH_2$, Ar—$(CH_2)_x$—$XCH_2$, $(CH_2)_x$—Ar—$(CH_2)_x$—$XCH_2$, Ar—$C(O)XCH_2$, $(CH_2)_x$—Ar—$C(O)XCH_2$, Ar—$(CH_2)_x$—$C(O)XCH_2$, $(CH_2)_x$—Ar—$(CH_2)_x$—$C(O)XCH_2$, $C(O)$—Ar—$XCH_2$, $C(O)$—$(CH_2)_x$—Ar—$XCH_2$, $C(O)$—Ar—$(CH_2)_x$—$XCH_2$, and $C(O)$—$(CH_2)_x$—Ar—$(CH_2)_x$—$XCH_2$, x is an integer of between 1 and 10, X is a member selected from the group consisting of O, S, and $NR^4$ where $R^4$ is H or $R^1$, X' is a member selected from the group consisting of O, S and NH, Ar and aryl are members selected from the group consisting of benzene, thiophene, furan, pyridine, pyrrole, imidazole, oxazole, thiazole, pyrazole, pyrimidine and cyclohexane rings and $R^2$ and $R^3$ are members selected from the group consisting of alkyl, aralkyl and alkaryl.

17. The polymer of claim 16 wherein n is 6 and m' is 11.
18. The polymer of claim 16 wherein n is 8 and m' is 15.
19. The polymer of claim 16 wherein n is 7 and m' is 13.

20. The polymer of claim 19 wherein X is O with the proviso that when a XC(O) moiety is present X is a member selected from the group consisting of O and NH.

21. The polymer of claim 19 where X' is O.

22. The polymer of claim 19 wherein Ar is phenylene.

23. The polymer of claim 18 wherein x is an integer of 1 to 5.

24. The polymer of claim 19 where the cyclodextrin is connected via the 3-position, p is 1, X' is 0, Q' is $CH_2O$—p—$C_6H_4$—$OCH_2$, R is $CH_2OCH_3$, $R^1$ is $CH_3$, e is 2 d is 0 $R^3$ is tolyl b is 50 and c is 5.

25. The polymer of claim 19 where the cyclodextrin is connected via the 2-position, p is 1, X' is 0, Q' is $CH_2O$—p—$C_6H_4$—$OCH_2$, n' is 7, R is $CH_2OCH_3$, m' is 13, $R^1$ is $CH_3$, e is 2, d is 0, $R^3$ is tolyl, b is 50 and c is 5.

26. The polymer of claim 19 where the cyclodextrin is connected via the 2-position, p is 1, X' is 0, Q' is $CH_2O$—p—$C_6H_4$—$OCH_2$, n' is 7, R is $CH_2OCH_3$, m' is 13, $R^1$ is $CH_3$, e is 2, d is 0, $R^3$ is tolyl, b is 50 and c is 5.

* * * * *